United States Patent [19]
MacKinnon et al.

[11] Patent Number: 6,110,106
[45] Date of Patent: Aug. 29, 2000

[54] ENDOSCOPES AND METHODS RELATING TO DIRECT VIEWING OF A TARGET TISSUE

[75] Inventors: Nicholas B. MacKinnon; Peter D. Whitehead, both of Vancouver, Canada

[73] Assignee: Biomax Technologies, Inc., Vancouver, Canada

[21] Appl. No.: 09/104,078

[22] Filed: Jun. 24, 1998

[51] Int. Cl.[7] .................................................. A61B 1/06
[52] U.S. Cl. ........................................ 600/181; 600/160
[58] Field of Search ..................................... 600/109, 160, 600/162, 166, 178, 179, 180, 181, 182, 183, 407, 473, 475, 476, 477, 478

[56] References Cited

U.S. PATENT DOCUMENTS

| | | |
|---|---|---|
| 4,045,125 | 8/1977 | Farges . |
| 4,151,411 | 4/1979 | Derderian et al. . |
| 4,595,262 | 6/1986 | Ogle . |
| 4,653,478 | 3/1987 | Nagasaki et al. .................. 600/109 |
| 4,718,417 | 1/1988 | Kittrell et al. . |
| 4,744,633 | 5/1988 | Sheiman . |
| 4,784,118 | 11/1988 | Fantone et al. .................. 600/160 |
| 4,821,116 | 4/1989 | Nagasaki et al. .................. 348/70 |
| 4,893,898 | 1/1990 | Beard . |
| 4,927,222 | 5/1990 | Kamiya et al. . |
| 5,001,556 | 3/1991 | Nakamura et al. .................. 348/70 |
| 5,144,344 | 9/1992 | Takahashi et al. . |
| 5,177,509 | 1/1993 | Johansen et al. . |
| 5,184,156 | 2/1993 | Black et al. . |
| 5,241,170 | 8/1993 | Field, Jr. et al. .................. 250/214 VT |
| 5,280,788 | 1/1994 | Janes et al. . |
| 5,304,173 | 4/1994 | Kittrell et al. . |
| 5,507,287 | 4/1996 | Palcic et al. .................. 600/317 |
| 5,590,660 | 1/1997 | MacAulay et al. .................. 600/478 |
| 5,647,368 | 7/1997 | Zeng et al. . |
| 5,701,903 | 12/1997 | Sano et al. .................. 600/478 |
| 5,733,246 | 3/1998 | Forkey .................. 600/160 |
| 5,891,016 | 4/1999 | Utsui et al. .................. 600/181 |

FOREIGN PATENT DOCUMENTS

| | | |
|---|---|---|
| 783 867 A1 | 7/1997 | European Pat. Off. . |
| WO 94/16622 | 8/1994 | WIPO . |
| WO 96/36273 | 11/1996 | WIPO . |
| WO 96/39925 | 12/1996 | WIPO . |

OTHER PUBLICATIONS

Zeng et al., Miniature spectrometer and multi–spectral imager as a potential diagnostic aid in dermatology. *SPIE Proceedings*, 2387:57–61, 1995.

Zeng et al., Spectroscopic and Microscopic Characteristics of Human Skin Autofluorescence Emission. *Photochemistry and Photobiology*, 61:639–645, 1995.

*Primary Examiner*—John P. Leubecker
*Assistant Examiner*—Brad C. Blaise
*Attorney, Agent, or Firm*—Graybeal Jackson Haley

[57] ABSTRACT

Apparatus and methods that permit the direct viewing of induced tissue fluorescence or other response by a human viewer through an endoscope without the need for bulky and expensive auxiliary apparatus such as imaging devices, sensor arrays, analyzing systems and computer hardware and software. The apparatus and methods provide an excitation energy, such as blue light, that is transmitted to the target, and then the endoscope collects the emitted response, which is typically fluorescent light of a wavelength longer than the UV or blue light used to induce the fluorescence. The endoscope then transmits the response through a series of filters in the endoscope and directly to the eye of a human user.

21 Claims, 15 Drawing Sheets

ENDOSCOPES AND METHODS RELATING TO DIRECT VIEWING OF A TARGET TISSUE

TECHNICAL FIELD OF THE INVENTION

The present invention relates to endoscopes for directly viewing a target, such as a target tissue in a human being.

BACKGROUND OF THE INVENTION

Point spectroscopy and spectral imaging of target tissue have been used to assess the condition of tissue in a patient, for example the presence of various illnesses or diseases. Such spectroscopy and imaging have used a variety of different techniques to effect such assessments, including absorbance spectroscopy in transmission and reflectance modes, fluorescence spectroscopy, and Raman spectroscopy (see, e.g., U.S. Pat. No. 4,836,203; U.S. Pat. No. 5,042,494; U.S. Pat. No. 5,062,428; U.S. Pat. No. 5,071,416; U.S. Pat. No. 5,421,337; U.S. Pat. No. 5,467,767; U.S. Pat. No. 5,507,287; Mahavedan-Jansen, A. and Richards-Kortum, R., *J. Biomed. Optics* $I(I)$:31–70 1996; U.S. Pat. No. 5,261,410). These techniques have been used in both single and multi-point measurements, and have been used in array spectroscopy to generate images on an imaging device such as a television screen.

A common form of array spectroscopy comprises the use of a color video camera in which a lens system projects an image through optical filters that select a desirable wavelength band or sub-region of the light forming the image, and then projects the image onto an array of sensors. The sensors convert the light into an electrical signal that is proportional to the light incident on a given sensor. The electrical signal can then be stored in a digital or analog format, and/or relayed directly to a device that displays the image, such as a color video monitor. This sort of a system where an image is captured by sensors, converted to electrical or other signals, and then re-created on a viewer (i.e., transduction of the original optical image to a different type of energy and then creation of a new image corresponding to the original image) is known as an imaging device or imager.

The color display monitor recreates an image viewable by a user by converting the electrical signals into optical signals. In this process, a color phosphor that emits light in a narrow wavelength region is stimulated by an amount proportional to the signal originally collected by its corresponding sensor. A conventional color monitor has red, green and blue phosphors. The wavelengths of light emitted by the phosphors of the monitor do not necessarily need to match the wavelengths of light that were collected by the sensors for the color to be perceived by the viewer as "normal." In particular, the photoreceptors of the human eye respond to only three wavelength regions, and colors perceived by humans only require that the eye be stimulated somewhere in a given wavelength response range for each of the red, green and blue photoreceptors of the eye.

Indeed, using such an imaging device, the colors received by the individual viewing the monitor do not necessarily have to bear any relationship to the wavelength of light originally perceived by the sensor. This property is often exploited with such devices as infrared cameras or x-ray or gamma cameras, where the sensors detect radiation that is well outside of the human visible range and then map the detected radiation to colors in the visible range. This use of imaging devices has also been applied to medical fluorescence imaging systems for detecting changes in the light emitted by tissue that has been illuminated with blue or ultraviolet light (or other light that induces a desired response). Imaging devices have been developed where the image sensors detect particular wavelength sub-ranges or bands of fluorescent light, process and scale the electronic signal, and then display the signal in two colors on a video monitor.

The methods and apparatus employed in using such imaging devices as described above require bulky systems including computers, television monitors and expensive sensors, analyzers and computer software and hardware. Such systems often also have a limited dynamic range. Accordingly, there has gone unmet a need for apparatus and methods that reduce the expense, bulkiness and/or complexity of, and increases the range for, viewing a target tissue. The present invention provides these and other related advantages.

SUMMARY OF THE INVENTION

The present invention provides methods and apparatus that permit the direct viewing of an induced tissue response by a human viewer without the need for bulky and expensive auxiliary apparatus such as imaging devices, sensor arrays, analyzing systems and computer hardware and software. Briefly, the present invention provides endoscopes, such as surgical microscopes, devices comprising monoculars or binoculars, colposcopes, fundascope and laparoscopes, that provide an excitation energy, transmit the excitation energy to the target, collect the emanated response light from the target, and transmit the emanated response light through a multi-function filter system in the endoscopes that selectively controls the ratio of the intensities of one or more wavelength bands of the emitted response. In many embodiments, the emanated response light is transmitted directly to the eye of a user without any transduction of the emanated response light. Thus, because several embodiments of the invention allow the user to look directly through the endoscopes to the target, there is no need for a video monitor or other types of transduction imaging devices such as those described above. Several embodiments of the present invention also provide multi-function, variable filter assemblies for use with such endoscopes as well as novel assemblies for varying the efficiency of the filter(s) disposed in the light path of such endoscopes and for identifying pre-selected filter strengths and filter combinations within such assemblies for given diseases.

Accordingly, in certain aspects the present invention provides endoscopes for directly transmitting an image from an in vivo target tissue to a user, the endoscope comprising: a body including a proximal end and a distal end, the body being configured to position the distal end proximate to the target tissue; a light emitter proximate to the distal end to direct an illumination light to the target tissue; an eyepiece ocular coupled to the body at the proximal end that is sized to fit a human eye; at least one collection light guide including a collector to receive emanating light from the target tissue and a conductor to conduct the emanating light along at least a portion of a light path to the eyepiece ocular; a wavelength selection filter aligned with the collection light guide to be disposed in the light path, the wavelength selection filter selectively transmitting at least two desired wavelength bands of the emanating light; and a wavelength ratio scaling filter aligned with the collection light guide to be disposed in the light path, the wavelength ratio scaling filter selectively controlling the intensity of at least one of the desired wavelength bands, the wavelength selection filter and the wavelength ratio scaling filter manipulating the emanating light from the target tissue to selectively enhance an image of the target tissue.

In preferred embodiments that relate to this and other aspects of the present invention (which is so for other preferred embodiments unless a given aspect of the invention indicates that such embodiment does not apply to that aspect), the collection light guide transmits the emanating light to the eyepiece, wherein the user is able to directly view the target tissue directly through the eyepiece ocular without a transduction imaging device between the target tissue and the user. In other preferred embodiments, the illumination light is conducted from a light source maintained at the proximal end of the endoscope to the light emitter at the distal end to of the endoscope via an illumination light guide, the light emitter is the distal end of the illumination light guide, or the light emitter comprises a light source disposed at the distal end of the endoscope.

In further preferred embodiments, the endoscope further comprises a band pass filter maintained at the distal end of the endoscope and disposed between the light emitter and the target tissue, wherein the band pass filter transmits a selected wavelength band of light. The selected wavelength band can be blue light able to induce fluorescence in the target tissue.

In still further preferred embodiments, the illumination light transmitted to the target tissue consists essentially of a selected wavelength band and the light collection system further comprises a long pass filter disposed in the light path, wherein the long pass filter blocks light having about the same wavelength as the selected wavelength band and transmits other light; the long pass filter can be disposed at the distal end of the light collection system and can block blue light if desired.

The wavelength selection filter can be maintained upstream in the light path from the wavelength ratio scaling filter, the long pass filter can be maintained upstream in the light path from the wavelength selection filter and the wavelength ratio scaling filter, and the long pass filter can be maintained upstream from the collection light guide which is maintained upstream from the wavelength selection filter which is maintained upstream from the wavelength ratio scaling filter.

In other preferred embodiments, one of the desired wavelength bands it green light and the wavelength ratio scaling filter is able to selectively vary the level of intensity of green light. In still other preferred embodiments, the endoscope is a surgical microscope, laparoscope, or colposcope.

In still other further preferred embodiments, the wavelength selection filter blocks at least wavelengths of light that are within the substantially overlapping photoreceptor response ranges of the human eye. Preferably, the wavelength ratio scaling filter is variable, further preferably continuously variable.

In other aspects the present invention provides endoscopes for directly transmitting an image from a target tissue to a user, the endoscope comprising: a body including a proximal end and a distal end, the body being configured to position the distal end proximate to the target tissue; means for emitting an illumination light from a location of the body at least proximate to the distal end; means for collecting and conducting an emanating light from the target tissue along a light path to an eyepiece sized to fit a human eye at the proximal end, wherein the means for collecting and conducting the emanating light filters the emanating light to conduct a first specific bandwidth of light at a first intensity and a second specific bandwidth of light at a second intensity to the eyepiece, such that a wavelength of light depicting an image of the target tissue is selectively enhanced.

In still other aspects the present invention provides methods for a user to directly view a target tissue through an endoscope, the methods comprising: a) illuminating the target tissue by emitting illumination light from a distal end of the endoscope to the target tissue under conditions suitable to thereby cause light to emanate from the target tissue to provide an emanating light; b) collecting the emanating light that contacts the distal end of a light collection system maintained in the endoscope; c) conducting the emanating light along a light path from the distal end of the endoscope to an eyepiece ocular at the proximal end that is sized to fit a human eye, wherein such conducting comprises transmitting the emanating light through a wavelength selection filter that selectively transmits at least two desired wavelength bands of the emanating light and through a wavelength ratio scaling filter that selectively controls the intensity of at least one of the desired wavelength bands to provide a filtered light representation of the target tissue; and, d) viewing the filtered light representation of the target tissue through the eyepiece ocular.

In certain preferred embodiments, the target is illuminated by conducting the illumination light from a light source maintained at the proximal end of the endoscope to a light emitter maintained at the distal end of the endoscope via an illumination light guide and then emitting the illumination light to the target tissue. In further preferred embodiments, the illumination light is transmitted through a band pass filter maintained at the distal end of the endoscope, wherein the band pass filter transmits a selected wavelength band of light and blocks other light. The selected wavelength band can be blue light able to induce fluorescence in the target tissue.

In other preferred embodiments, the illumination light emitted from the light emitter consists essentially of a selected wavelength band and the light collection system further comprises a long pass filter disposed in the light path, wherein the long pass filter blocks light having about the same wavelength as the selected wavelength band and transmits other light.

In further preferred embodiments, the one of the desired wavelength bands is green light and the wavelength ratio scaling filter is able to selectively vary the level of intensity of green light. In further some preferred embodiments, the illumination light is selected to cause a detectable response in an exogenous fluorophore in a desired drug potentially found in the target tissue, and the viewing comprises determining the presence or amount of the drug in the tissue. The methods discussed herein can be performed using an endoscope as also described herein.

In still further aspects the present invention provides methods for a user to directly view a target tissue through an endoscope, the method comprising the following steps: a) the step of illuminating the target tissue by emitting illumination light from a distal end of the endoscope to the target tissue under conditions suitable for causing light to emanate from the target tissue to provide an emanating light; b) the step of collecting the emanating light that contacts the distal end of a light collection system maintained in the endoscope; c) the step of conducting the emanating light along a light path from the distal end of the endoscope to an eyepiece ocular at the proximal end that is sized to fit a human eye, wherein such conducting comprises transmitting the emanating light through a wavelength selection filter that selectively transmits at least two desired wavelength bands of the emanating light and through a wavelength ratio scaling filter that selectively controls the intensity of at least one of the desired wavelength bands for providing a filtered light representation of the target tissue; and, d) the step of viewing the filtered light representation of the target tissue through the eyepiece ocular.

In still other further aspects the present invention provides endoscopes for directly transmitting an image without transduction from an in vivo target tissue to a user, the endoscopes comprising: a proximal end and a distal end and an elongated body therebetween; a light emitter at the distal end able to emit illumination light consisting essentially of blue light to the target tissue; a light collection system able to collect emanating light that contacts the distal end and conduct the emanating light along a light path to an eyepiece ocular at the proximal end that is sized to fit a human eye, wherein the light collection system comprises at least one collection light guide able to conduct the emanating light along at least a portion of the light path, a long pass filter disposed at the distal end of the collection light guide and that substantially blocks blue light, a wavelength selection filter disposed in the light path and able to selectively transmit at least two desired wavelength bands of the emanating light, and a wavelength ratio scaling filter disposed in the light path and able to selectively control the intensity of at least one of the desired wavelength bands, and wherein the user is able to directly view the target tissue through the eyepiece ocular without an imaging device between the target tissue and the user.

In some preferred embodiments, the illumination light is conducted from a light source maintained at the proximal end of the endoscope to the light emitter at the distal end of the endoscope via the illumination light guide, and wherein a band pass filter that transmits substantially only blue light is disposed at the distal end of the illumination light guide.

In still more aspects the present invention provides filter assemblies for a scope to transmit an image from an in vivo target tissue to a user, comprising: a casing including a proximal end with a first opening to receive a proximal section of the scope, a distal end with a second opening to receive a distal section of the scope, and a transmission passage extending between the first and second openings, the transmission passage being configured to transmit light along a light path from the distal end to the proximal end of the casing; a rotatable housing attached to the casing, the rotatable housing including a knob configured to be gripped by a user and a filter holder positioned in the casing, the filter holder having a plurality of windows; and, at least one filter received in one of the windows, the housing rotating within the casing to position the at least one filter in alignment with the light path for selectively enhancing an image of the target tissue.

In some preferred embodiments, the at least one filter disposed within the at least one wall of the filter assembly is able to transmit at least two discrete desired wavelength bands of the light, and/or the filter assembly comprises at least two of the housings, at least one housing having a wavelength selection filter disposed in the light path that is able to selectively transmit the at least two discrete desired wavelength bands, and at least one housing having a wavelength ratio scaling filter disposed in the light path and able to selectively control the intensity of at least one of the desired wavelength bands.

In other preferred embodiments, the filter assembly further comprises a non-rotatable lens that maintains the sharpness of an image being transmitted along the light path and disposed in the light path within the housing. The filter assembly can be sized to be placed within an endoscope, and/or it can be included in an endoscope disclosed herein.

These and other aspects of the present invention are discussed further in the following Detailed Description and the attached drawings. In addition, various references are set forth herein that describe in more detail certain procedures or apparatus, etc. (e.g., endoscopes, etc.); all such references are incorporated herein by reference in their entirety.

DETAILED DESCRIPTION OF THE INVENTION

Figure 1:
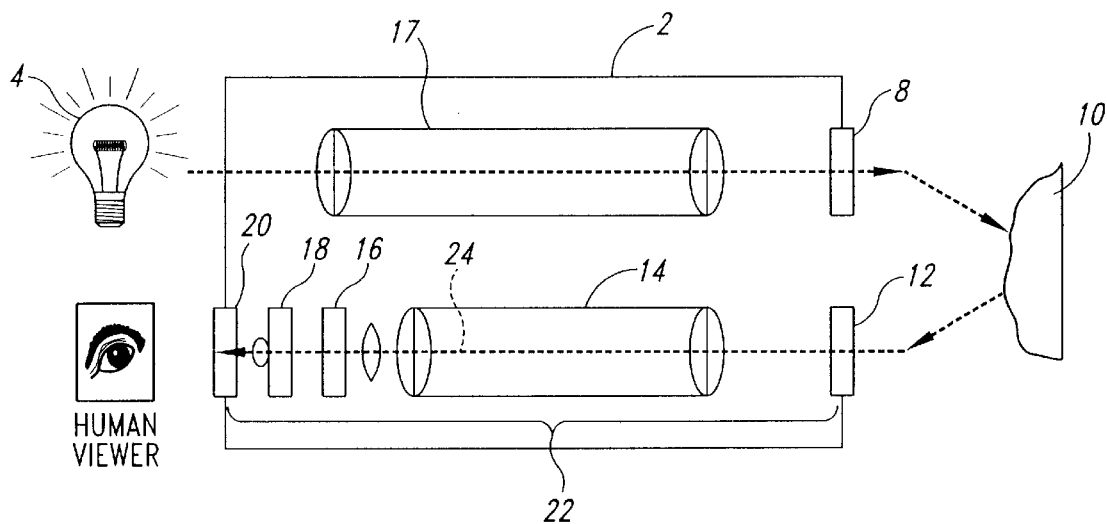
FIG. 1 is a schematic diagram of an endoscope system according to an embodiment of the present invention that permits direct viewing of a target tissue by a human viewer.

The present application discloses methods and apparatus that permit the direct viewing of induced tissue fluorescence by a human viewer without the need for bulky and expensive auxiliary apparatus such as imaging devices, sensor arrays, analyzing systems and computer hardware and software. Briefly, several embodiments of the present invention include endoscopes that are suitable for viewing an internal target, such as a target tissue that is either related to, or is actually tissue of the heart, lungs, liver, skin, throat, lymph nodes, hair, intestines or cervix. The endoscopes provide an excitation energy, such as blue light, that is transmitted to the target, and then the endoscopes collect the emanated response light returning from the target, which is typically fluorescent light of a wavelength longer than the UV or blue light used to induce the fluorescence. The endoscopes then transmit the response light through a series of filters in the endoscopes and directly to the eye of a human user. Because the user can look directly through the endoscopes to the target, there is no need for a transduction imaging device such as those described herein. The viewer is also able, because transduction of the image is not performed, to view the target tissue with the full range of sensitivity of the human eye, thereby providing a greater dynamic range for analyzing the target tissue. As used herein, the term "light" includes electromagnetic radiation having a wavelength from at least ultraviolet radiation through infrared radiation. Thus, the term "light" is not limited to "visible light."

The filters through which the images pass include a wavelength ratio scaling filter that allows the user to select a specific intensity for a desired wavelength band, thereby increasing or decreasing the intensity of that band of light relative to one or more other desired wavelength bands. Preferably, the user can vary the intensity of the wavelength band using a single filter assembly. This ability to control the ratio of the intensities of the wavelength bands permits the user to optimize the effectiveness of his or her assessment of the target.

Turning to a general discussion of the apparatus and methods of the invention, an "endoscope" is a generally tubular device for insertion into a body, typically via canals, vessels, passageways or body cavities for any of a variety reasons, such as diagnostic purposes, the injection or withdrawal of fluids or to keep a passageway open. As used herein, an endoscope is an in vivo optical viewer for viewing internal targets (such as internal organs) and includes other such internal, in vivo optical viewers such as laparoscopes, fundascopes, colposcopes, otoscopes and surgical microscopes. An endoscope is similar to a catheter, except that generally an endoscope is considered to transmit an image while a catheter does not; for the purposes of the present specification, the term endoscope includes catheter unless otherwise clear from the context. The endoscope is preferably rigid, but can be flexible. The discussion herein regarding endoscopes also generally applies to other types of in vivo optical viewers, including viewers for external use such as otoscope-like viewers for examining the skin, unless clear from the context.

The distal end of an endoscope is the end of the endoscope that is inserted into the body and directed to a target tissue; the proximal end is the end of the endoscope that is maintained outside the body, and typically comprises an ocular eyepiece and one or more handles, knobs and/or other control devices that allow the user to manipulate the distal end of the endoscope or devices located at the distal end of the endoscope. As used herein, the distal end of the endoscope includes the distal tip of the endoscope, which is the most distal surface or opening of the endoscope, and the portion of the endoscope adjacent to the distal tip of the endoscope. Endoscopes generally are well known. U.S. Pat. No. 5,409,000; U.S. Pat. No. 5,409,009; U.S. Pat. No. 5,259,837; U.S. Pat. No. 4,955,385; U.S. Pat. No. 4,706,681; U.S. Pat. No. 4,582,061; U.S. Pat. No. 4,407,294; U.S. Pat. No. 4,401,124; U.S. Pat. No. 4,204,528; U.S. Pat. No. 5,432,543; U.S. Pat. No. 4,175,545; U.S. Pat. No. 4,885,634; U.S. Pat. No. 5,474,519; U.S. Pat. No. 5,092,331; U.S. Pat. No. 4,858,001; U.S. Pat. No. 4,782,386; U.S. Pat. No. 5,440,388. Endoscopes comprising optical probes and methods of analyzing scans using the same are also well known in the art. U.S. Pat. No. 5,421,337; U.S. Pat. No. 5,507,287; U.S. Pat. No. 5,467,767; U.S. Pat. No. 5,071,416; U.S. Pat. No. 5,042,494; U.S. Pat. No. 5,062,428; U.S. Pat. No. 4,836,203; U.S. Pat. No. 4,845,552; EP 0/595,506; WO 95/26673 and U.S. application Ser. No. 09/039,279 filed Mar. 12, 1998; U.S. provisional patent application No. 60/040,557, filed Mar. 13, 1997, U.S. provisional patent application No. 60/046,368, filed May 15, 1997, and U.S. provisional patent application No. 60/053,688, filed Jul. 25, 1997, all of which are presently pending.

Endoscopes generally comprise a light source, or other electromagnetic energy source, that provides illumination, light that is emitted from the distal end of the endoscope, and shined on the target, thereby making it possible to visualize the target. The light source itself can be maintained either at the distal end or the proximal end of the endoscope; when the light source is maintained at the proximal end, or elsewhere upstream from the ejection point of the light, the endoscope typically comprises at least one illumination light guide that conducts the light from the light source to the distal end of the endoscope. The ejection point of the light, therefore, is referred to herein as an "emitter," which can be an active light source or an optically transmissive element that projects light from an active light source. In many applications, the light guide is a fiber optic strand or a bundle of fiber optic strands. In some embodiments, the illumination light is filtered, typically at the distal end of the endoscope.

The endoscopes also comprise a light collection system comprising at least one collection light guide, a multi-function filter system that typically comprises a plurality of filters, and an eyepiece ocular. The filters are preferably disposed on or comprise an equivalent plurality of substrates (such as optically clear glass or plastic or an absorbance filter such as a long pass filter), but can be disposed on a lesser number of substrates, or even a single substrate if desired. In addition, for example where the filter comprises an angularly adjustable filter (discussed further below), a single filter can be adequate for use in the present invention provided that the necessary plurality of functions is maintained. The collection light guide (and/or other optical devices disposed at the distal end of the collection light guide such as a filter or lens) collects light that returns from the target tissue. The light returning from the target can be reflected light or fluorescent light, and it is referred to herein as emanating or collected light.

The collection light guide transmits the emanating light along at least a portion of a light path toward the proximal end of the endoscope; the light path is defined herein as the path of the light from the distal tip of the endoscope, or first reception of the emanating light into the endoscope if the light collector is not maintained at the distal tip, to the proximal end of the endoscope where the light is presented at an eyepiece ocular for direct viewing by a user. Thus, in many aspects of the invention, the light path provides for direct transmission of the image of the target tissue from such tissue to the user without any transduction imaging device interspersed in the light path. Please note, however, that in some embodiments of the present invention a transduction imaging device can be attached to the endoscope for a secondary viewing option of the target tissue, but such transduction imaging device is still not typically maintained within the light path for the purposes of the present invention because such transduction imaging device does not create the image provided in the eyepiece ocular. The eyepiece ocular is a viewing site for the user and is typically a monocular eyepiece, but it can be binocular or a piece of ground glass that functions as a viewscreen or other direct viewing device.

The illumination light guide and the collection light guide can be a single light guide, which means that the same light guide can function as both the illumination light guide and the collection light guide. Alternatively, the illumination light guide and the collection light guide can be separate light guides. In a preferred embodiment, the illumination and/or collection light guides comprise a focusing device at their downstream (i.e., distal end or proximal end, respectively), for example a gradient refractive index (GRIN) lens, a microlens, or a diffractive optic lens. Typically, the light guide can be an optical fiber, fiber bundle, liquid light guide or hollow reflective light guide or lens system, or other pathway suitable for carrying the image of the target from the distal end to the proximal end of the endoscope. The light path can also comprise, or consist of, a hollow air-filled casing, for example in an otoscope or otoscope-like instrument. Each of the illumination light guide and the collection light guide are able to conduct light along at least a portion of its relevant light path. For example, the collection light guide can transmit the emanating light from the distal end to the proximal end of the endoscope; if all filters and optical elements are disposed between the two ends of the collection light guide, then the collection light guide is deemed to conduct the emanating light along the entire light path from the distal end of the endoscope to the ocular eyepiece at the proximal end of the endoscope. On the other hand, if one or more of the filters or other optical elements disposed in the light path are disposed either before or after the collection light guide (i.e., upstream or downstream, respectively), then the collection light guide conducts light along a portion of the light path. (Upstream means that the filter is disposed near the distal end and downstream means that the filter is disposed near the proximal end of the collection light guide; the upstream direction would be near the proximal end for the illumination light guide.)

The light collection system comprises at least one wavelength selection filter and at least one wavelength ratio scaling filter. These filters are disposed in the light path of the emanating light, which means that the filters can be disposed either upstream, downstream or between the ends of the collection light guide.

The wavelength selection filter is a light filter that is able to selectively transmit at least two desired wavelength bands while blocking light with wavelengths outside of the wavelength bands. The wavelength selection filter will accordingly transmit at least two different wavelength bands of light in well-defined ranges while blocking other light, preferably 100% of other light. Preferably, the wavelength selection filter is similar to a band pass-type filter, wherein the wavelength selection filter transmits the desired wavelengths bands and no other light. Such filters are well known in the art and can be obtained, for example, from Melles-Griot, Irvine, Calif.; Ealing Electro-Optical, Inc., Holliston, Md.; Corion, Brattleboro, N.H., or the filters can be custom made according to the desires of the user.

The two or more desired wavelength bands can be immediately adjacent to each other along the continuum of wavelengths of electromagnetic radiation, although preferably there is a wavelength gap between the two wavelength bands that is blocked so as to accentuate the differentiation of the two wavelength bands, thereby providing two discrete wavelength bands. The desired wavelength bands are defined to be any two or more specific bands of light that are desired by the user, typically two or more of blue light, green light and red light, preferably red light and green light for some embodiments. Typically, a single desired wavelength band is from about 5–200 nm in width.

In a preferred embodiment, particularly where the examination of the target comprises the induction of fluorescence in the target, the wavelength selection filter transmits red and green light and blocks, among other bands, a substantial portion, and preferably all, of the blue light and ultraviolet light. With the use of such filter, the fluorescence can be induced using a blue light or UV light excitation source (preferably a blue light excitation source in order to reduce the likelihood of damage to the tissue from the excitation light), and then the wavelength selection filter blocks out any reflectance (blue or UV) light, thereby transmitting only fluorescent light.

In another preferred embodiment, the wavelength selection filter blocks a substantial portion, and preferably all, wavelengths of light that are within the overlapping photoreceptor response ranges of the human eye. (See FIG. 2.) Typically, such filters block from about 530 nm to about 560 nm, and at least one other wavelength band, which second band can vary according to the desires of the user.

Some preferred combinations of illumination light and desired wavelength bands include those wherein the illumination light is blue or UV light that induces fluorescence, the desired first and second wavelength bands are from (a) about 480 nm–530 nm and (b) about 560 nm–725 nm or longer, respectively. In another embodiment, for example where the illumination light is UV light such as 380 nm, the desired first and second wavelength bands are from (a) about 400 nm–440 nm (i.e., blue light) and (b) about 530 nm/560 nm—to any longer wavelength, respectively; if the illumination light is increased to about 400 nm–405 nm, then the desired first wavelength band (a) is increased to about 420 nm/440 nm. In another preferred embodiment, the illumination light is about 380 nm–410 nm and the desired first and second wavelength bands are from (a) about 410 nm–440 nm and (b) about 480 nm–520 nm (i.e., from about 440 nm–480 nm and from about 520 nm and longer are blocked). In another embodiment, known as multi-photon induction of fluorescence and discussed further below, the effective wavelength of the illumination light is the same as discussed above, but the actual wavelength is 2× (or other multiple) the effective wavelength; the desired wavelength bands remain the same.

The wavelength ratio scaling filter selectively controls the ratio of the intensities of the two or more desired wavelength bands that are transmitted by the wavelength selection filter. Typically, the wavelength ratio scaling filter selectively controls the ratio by attenuating or diminishing one or more of the desired wavelength bands. The wavelength ratio scaling filter preferably filters at least a wavelength band of light that is slightly greater in width than the selected desired wavelength band that it is filtering (thus, the wavelength ratio scaling filter preferably acts on a band of light that is "overlapping" relative to the selected desired wavelength band that has been transmitted by the wavelength selection filter). Preferably, the degree that the desired wavelength band is selectively controlled by the wavelength ratio scaling filter can be varied by "dialing in" or otherwise tuning in a desired level of filtering. This "variable filtering" by the wavelength ratio scaling filter can be effected, for example, via the use of rotatable filters and/or a plurality of filters that can be selectively interspersed in the collection light path. Examples of suitable wavelength ratio scaling filters are disclosed in FIGS. 3–8 and discussed further below.

Figure 9A:
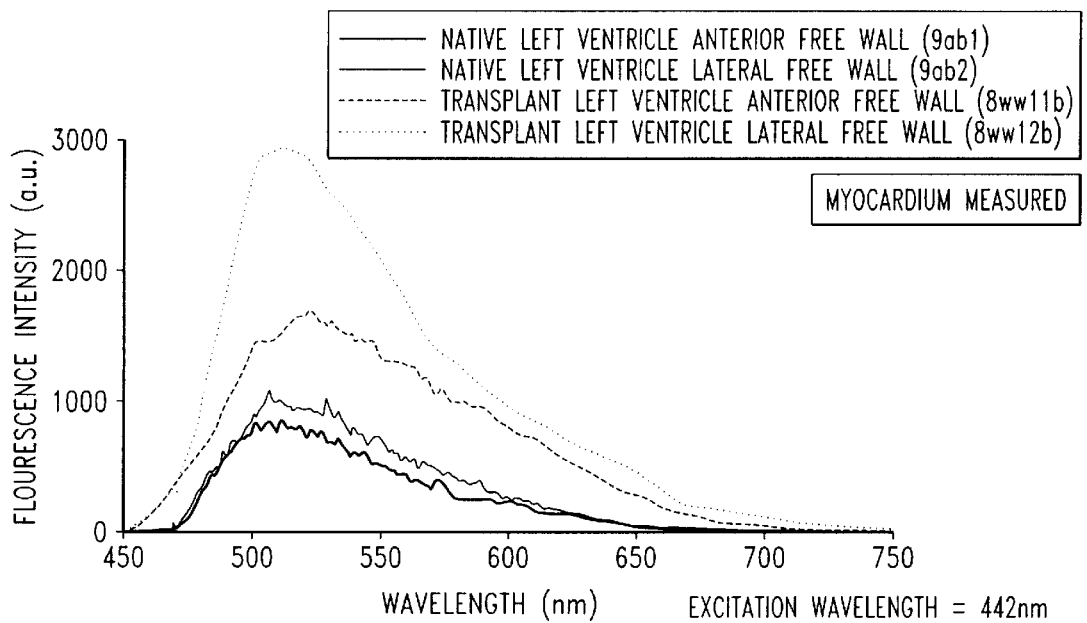
FIGS. 9A and 9B are graphs illustrating fluorescence spectra from a transplanted rat heart and a control rat heart.
Figure 9B:
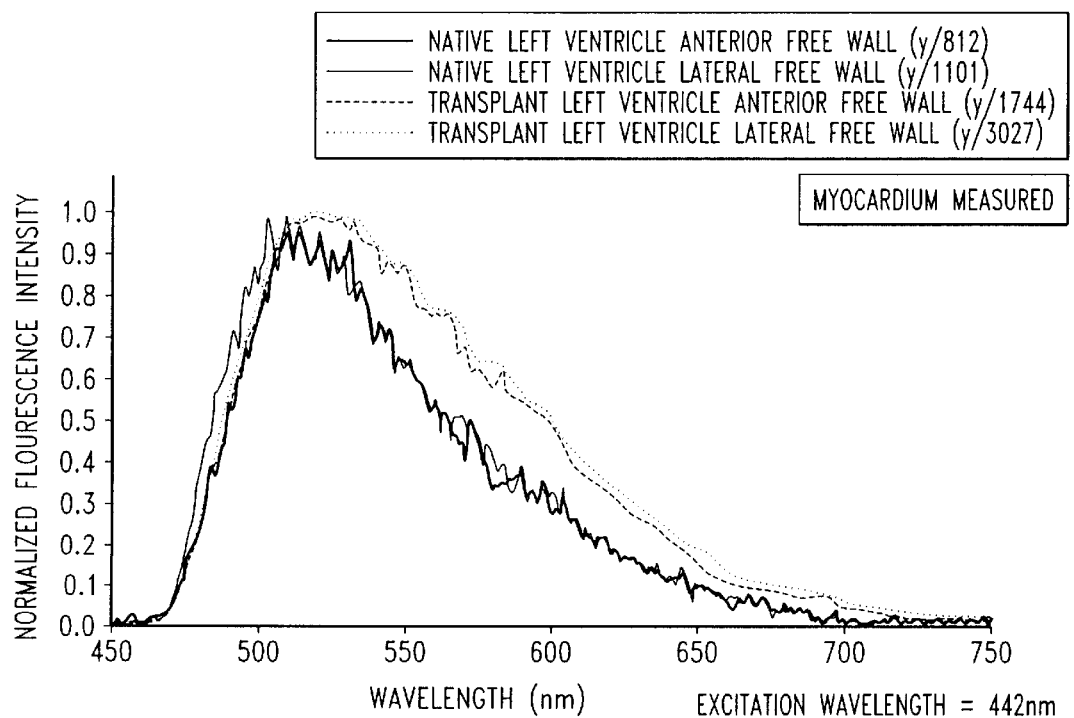

In one embodiment, such as where the emanating light comprises fluorescence light induced by a blue or UV illumination light, the wavelength ratio scaling filter attenuates green light. For example, and as discussed further below, in an induced fluorescence spectrum of either healthy and non-healthy tissue, the intensity of the green light generally predominates the intensity of the red light. A red-shift of the spectrum (i.e., a general shift of the spectrum to longer wavelengths) indicates that the target tissue is diseased or otherwise potentially non-healthy. For example, FIGS. 9a–9b depict examples of such fluorescence spectra for tissue undergoing rejection. See also U.S. patent application Ser. No. 09/041,861, entitled Methods and Apparatus for Detecting the Rejection of Transplanted Tissue and filed Mar. 12, 1998 and references cited therein. By reducing the intensity of the green light relative to the red light, the red-shift of the spectrum can be more easily discerned. In preferred embodiments, the wavelength ratio scaling filter variably attenuates between about 2% to 98% of the intensity of the green light in the emanating light that is collected from the target tissue. In other embodiments, which can also be useful for detecting disease or other potentially non-healthy situations, the wavelength ratio scaling filter preferably variably attenuates blue, yellow or red light.

The particular filter or filter combination that is in the light path in the in vivo optical viewer can be indicated to a user by markings in or on the filter assembly. For example, the labels can be disposed on the side of a disk that contains a plurality of different filters or on a knob that is visible to the user and used to select different filter combinations. In one embodiment, the markings indicate particular filter transmission levels, band widths, and/or other optical information about the filters. In a preferred embodiment, such markings comprise identifiers for specific diseases, thereby providing the user the ability to dial in a specific disease for which a specific filter combination is known. For example, with the disease psoriasis, there is an extra peak at about 635 nm in the fluorescence that is emitted from the disease site. A filter combination that enhances the ability of the user to see this peak is one preferred combination and could therefore be dialed in merely by pointing the dial to "psoriasis." Other preferred combinations comprise filters that enhance the visibility of wavelength bands absorbed by blood (e.g., about 540 nm±10 nm and about 580 nm±10 nm) for situations where the user desires to find or avoid blood vessels, or combinations that block such wavelengths where absorption by blood is an interference to the desired viewing. Other preferred combinations enhance the visibility of wavelength bands associated with desired photo-activated drugs.

In one preferred embodiment, typically where the present invention comprises a kit, a plurality of different filters/filter assemblies can be readily input and removed from the endoscope, and the invention provides a storage rack or other framework that holds or retains the different filters and/or multi-filter assemblies (such as the filter wheels and disks depicted in FIGS. 3–8) when they are not in place in the endoscope and/or the plurality of different filters/filter assemblies themselves. The filters/filter assemblies can be identified by identification marks (e.g., labels, etching) attached to or imprinted upon the filters/filter assemblies themselves and/or to dedicated slots or spaces in the rack that are specific for given filters/filter assemblies.

In another preferred embodiment, the present invention provides hand-held in vivo optical viewers that can be similar to an otoscope; such a device can be used for either internal or external review of a patient, depending upon the desires of the user. The device can be either battery powered or connected via electrical leads to an external power source. In one preferred embodiment, the device is battery powered by rechargeable batteries that are automatically recharged upon placement of the device into a recharging stand. In a preferred embodiment, this hand-held device comprises light emitting diodes (LED's) at the distal end of the viewer, which LED's emit desired wavelength(s) of light.

Where such a hand-held device is to be used external to the body, the device is preferably used in a darkened room. Alternatively, the distal end of such a viewer can comprise a hollow, substantially tubular extension (which can also house the other components of the in vivo optical viewer as discussed herein) that is suitable for contact with the skin or other external surface under investigation. In preferred embodiments, the distal end of such a tubular housing forms an angle relative to the light path such that the in vivo optical viewer is held in contact with the skin (or other target site) at an angle other than perpendicular, for example a 45° angle to the skin. This can reduce the amount of reflectance light that enters the light collection system of the viewer. In addition, the internal surface of the tubular housing can be white, black or a specific selected color, if desired.

In a preferred embodiment, the endoscopes of the present invention also comprise at least one band pass filter disposed at the distal end of the illumination light guide. Such a filter is particularly preferred where the illumination light is a narrow wavelength band, such as a laser light consisting essentially of blue light or UV light for induction of fluorescence in the target, which means light in which there is little enough non-blue light that such light does not prevent clinical use of the endoscope. By definition, a band pass filter transmits a selected bandwidth of light, which means a predetermined wavelength or set of wavelengths, and blocks other light, preferably 100% of other light. Band pass filters are well known in the art and can be obtained from Melles-Griot, Irvine, Calif.; Ealing Electro-Optical, Inc., Holliston, Md.; Corion, Brattleboro, N.H., or the filters can be custom made according to the desires of the user. Typically, the band pass filter will transmit a selected bandwidth of about 20–200 nm in width, although other bandwidths are known in the art and can be selected by a person of ordinary skill depending upon the desired properties in view of the present specification.

The endoscopes of the present invention also preferably comprise a long pass filter in the light collection system, further preferably located at the distal end of the light collection system. Such a long pass filter in the light collection system could instead be a band pass filter or a short pass filter for certain embodiments, such as the use of multi-photon-type illumination light. The long pass filter blocks known non-desirable wavelength bands emanating from the target, particularly if such wavelength bands are capable of inducing fluorescence in the collection light guide or otherwise introducing increased noise, interference or other artifact in the light collection system. Thus, the long pass filter is preferably disposed at the distal end of the light collection system because the long pass filter can then block undesired wavelengths of light, such as fluorescence-inducing excitation light, prior to its entering the collection light guide and potentially causing fluorescence therein. Long pass filters are well known in the art and can be obtained, for example, from Melles-Griot, Irvine, Calif.; Ealing Electro-Optical, Inc., Holliston, Md.; Corion, Brattleboro, N.H., or the filters can be custom made according to the desires of the user.

As noted above, some preferred methods and apparatus of the present invention comprise the induction and viewing of fluorescence in a target tissue. This is because healthy tissue exhibits a characteristic fluorescence response in reply to excitation with electromagnetic radiation having a wavelength in the ultraviolet to visible light ranges, while the fluorescence response of diseased, injured or otherwise harmed tissue changes relative to the healthy tissue. The illumination or excitation light energy that is transmitted to the target tissue typically comprises light from ultraviolet light through visible light and can induce fluorescence, reflectance or other response in the target tissue. Preferably, the light does not comprise UV light because such light can be harmful to the tissue. Conditions to induce fluorescence in tissue are well known in the art. See, e.g., U.S. Pat. No. 4,836,203; U.S. Pat. No. 5,042,494; U.S. Pat. No. 5,062,428; U.S. Pat. No. 5,071,416; U.S. Pat. No. 5,421,337; U.S. Pat. No. 5,467,767; U.S. Pat. No. 5,507,287.

Fluorescence and fluoresce are used herein in their ordinary sense, which includes the emission of, or the property of emitting, electromagnetic radiation, typically in the visible wavelength range, resulting from and occurring after the absorption of the illumination or excitation light that is transmitted to the transplanted tissue. Fluorescence includes fluorescent light produced by either endogenous fluorophores or exogenous fluorophores; exogenous fluorophores include those provided by drugs, chemical labels or other external sources. Autofluorescence is fluorescence from endogenous fluorophores. The fluorescence is collected, or gathered, from the target tissue so that it can be analyzed to provide a target fluorescent image, which means a particular fluorescent image for that particular target tissue.

Fluorescence characteristics that contribute to the changes observable in target tissue undergoing a specific disease state or other condition are affected by the wavelength of excitation, and the concentration, absorption coefficients, scattering coefficients, quantum efficiency, and the emission spectra of the fluorophores inside the tissue. For example, in vivo determination of the presence or absence of characteristics of rejection of a target heart preferably includes viewing the endocardium, epicardium, myocardium and/or arterial tissue for the fluorescence characteristics described above, as well as changes in fluorescence characteristics due to physiological changes associated with rejection such as thickening of the endothelium and increase in collagen content.

Different wavelengths of illumination or excitation light can excite different fluorophores inside a target tissue, and therefore can lead to different quantum efficiencies for exciting tissue fluorescence. Thus, the user can select one or more desired excitation wavelengths in order to achieve better or more complete detection sensitivity. In one preferred embodiment, a laser excitation light system is used for various excitation wavelengths because such a system conveniently facilitates utilizing excitation wavelengths from about 360 nm UV to about 700 nm IR.

In addition to using different single wavelengths of illumination light, multiple wavelengths of illumination light can be used simultaneously or sequentially, thereby providing at least two photons of different wavelengths for absorption by the target tissue. For example, combining simultaneous excitation by one photon at 800 nm with excitation by a second photon at 1000 nm can provide enhanced detection because the longer wavelength light can penetrate deeper into the tissue to sample a large tissue volume. In addition, different fluorophores may be excited, and the absorption of the fluorescence spectra by interfering matter can be reduced.

In one preferred embodiment, the induction of fluorescence comprises the simultaneous excitation of the fluorophore by multiple photons, each having a certain fraction of the energy of a single photon at the desired excitation wavelength. In particular, when the multiple photons (which are at a longer wavelength) simultaneously contact the fluorophore, the energies of the photons combine to provide the same excitation that is achieved by the use of a single photon at a shorter wavelength. An advantage of this approach is that the longer wavelength, lower energy photons can penetrate deeper into the tissue, and therefore sampling can take place at different and/or deeper tissue depths. Typically, this multi-photon excitation is effected using two photons that each have one-half the energy of the desired photon, although it is possible to use three photons each having one-third the energy, etc. The resulting fluorescence is the same as the fluorescence induced using other excitation methods discussed herein, and therefore the analysis of the fluorescence is also the same.

In another aspect, the present invention provides methods for directly viewing a target tissue through an endoscope or other in vivo optical viewer. These methods are preferably performed using the endoscopes described herein. The methods comprise illuminating the target tissue by emitting illumination light from a distal end of an endoscope to the target tissue under conditions that are suitable to cause light to emanate from the target tissue. As noted above, such light that emanates from the target tissue is termed "emanating light." A portion of the emanating light contacts the distal end of a light collection system that is maintained in the endoscope, and is then collected or gathered by such light collection system. The light is then conducted along a light path from the distal end of the endoscope to an eyepiece ocular at the proximal end of the endoscope, where the light is available for viewing by a user.

The light is passed through a wavelength selection filter that selectively transmits at least two desired wavelength bands of the emanating light and through a wavelength ratio scaling filter that selectively controls the intensity of at least one of the desired wavelength bands to provide a filtered light representation or image of the target tissue. The filtered light representation is a direct optical representation of the target tissue, as opposed to a spectrograph or other scan of the target tissue. In addition, the filtered light representation or image is a direct image, as opposed to an image created by transduction in an imaging device. The methods then comprise viewing the filtered light representation of the target tissue through the eyepiece ocular without an imaging device between the target tissue and the eyepiece. In preferred embodiments, the target is illuminated by conducting the illumination light through a band pass filter maintained at the distal end of the endoscope, which filter transmits the selected wavelength band of illumination light and blocks other light, for example to eliminate interfering fluorescence derived from the illumination light guide itself. In addition, the emanating light is preferably collected through a long pass filter disposed at the distal end of the endoscope, which long pass filter eliminates unwanted light such as reflectance light from the illumination light.

In another embodiment, the methods, in addition to or in place of certain other steps discussed herein, comprise selecting a particular filter combination (i.e., a particular set of a desired wavelength selection filter and a desired wavelength ratio scaling filter) for a specific purpose by choosing a setting for the filters that is identified by one or more labels or other markings reciting one or more specific diseases or other conditions for which the particular filter combination is appropriate. The particular filter combination that is thus selected can be chosen, for example, by rotating a disk comprising a plurality of desirable filters and having disposed on the side thereof the labels identifying the disease(s) or other condition(s), by turning a knob that is visible to the user has such labels on its top or side, or by selecting the filter or multi-filter holder (such as a filter wheel comprising a plurality of filters) from a rack that stores and identifies a plurality of such filters/multi-filter holders. In one embodiment, the markings indicate both the condition(s) and specific strengths, band widths, and/or other optical information about the filters.

In another preferred embodiment, which comprises the use of a hand-held in vivo optical viewer, which viewer can be either battery powered or connected via electrical leads to an external power source, the methods comprise picking up the in vivo optical viewer in the hand of a user, placing the distal end of the viewer near a target site, such as the skin or ear canal, placing at least one eye of the user in position to view the target site through the viewer, illuminating the target site using the illumination source associated with the viewer, and then viewing the target site through the in vivo optical viewer and evaluating the target site and determining whether the target site comprises a given disease or other condition. The precise order of these steps can be varied according to the desires of the user. In a preferred embodiment, the steps further comprise selecting the desired particular filter combination using the methods discussed above.

In other preferred embodiments, the viewer is battery powered and the methods further comprise recharging the viewer by placing it onto a stand. In still other preferred embodiments, where the distal end of the viewer comprises a hollow tubular extension that is suitable for contact with the skin or other external surface under investigation, the methods further comprise contacting the distal edge of the housing with the target site (or the skin or other surface surrounding the target site if such site is smaller than the diameter formed by the housing); this aspect of the methods can be performed in a fully lighted room, if desired, and therefore if desired does not include turning off the ambient lighting, at the option of the user.

Turning to the Figures, FIG. 1 is a schematic diagram of one embodiment of an endoscope according to the present invention. In particular, light source 4 is maintained at the proximal end of endoscope 2, and light from light source 4 is projected into the proximal end of illumination light guide 7. Exemplary proximal-end light sources and their connection to an illumination light guide are described schematically in FIGS. 10–12. In other embodiments, the light source 4 is located at the distal end of the endoscope 2. Exemplary distal-end light sources are described schematically in FIGS. 13–16.

In FIG. 1, the light from light source 4 is conducted by illumination light guide 7 to the distal end of endoscope 2, where band pass filter 8 filters out at least substantially all undesired wavelengths of light and transmits the desired bandwidth of light. The location of band pass filter 8 at the distal end is preferred where the illumination light comprises or consists essentially of light that can induce artifacts in the illumination light guide (such as fluorescence from the illumination light guide itself); the band pass filter 8 blocks such artifacts from reaching the target. The illumination light is then directed from band pass filter 8 to tissue 10. Thus, in the embodiment depicted in FIG. 1, band pass filter 8 acts as a light emitter for endoscope 2; if no band pass filter is disposed at the distal end of endoscope 2, then the distal end of illumination light guide 7, or an alternative desired optical element (if any) disposed at the distal end of endoscope 2, acts as the light emitter. The light emitter, therefore, can be an active light source that generates the light, or the light emitter can be a passive transmissive element that projects the light.

Upon entering tissue 10 (or other target) the illumination light causes a response in tissue 10, which response is an emanating light comprising reflectance light, fluorescence light, and/or other light-induced responses. In a preferred embodiment, the light source 4 is a blue light excitation source, and the distal end band pass filter 8 transmits only blue light of about the wavelength emitted by light source 4. When the light source 4 is an appropriate light source, fluorescence is induced as the response in target tissue 10. Target tissue 10 then emits its response as emanating light or other electromagnetic energy.

The light emanating from tissue 10 contacts the distal end of light collection system 22, which is maintained in endoscope 2. The emanating light travels along light path 24 through a long pass filter 12 maintained at the distal end of the light collection system 22, which long pass filter, in a preferred embodiment, eliminates reflectance light from the excitation light source 4. Collection light guide 14 then conducts the emanating light to an emission wavelength selection filter 16, which filter 16 selectively transmits at least two desired wavelength bands. The light then continues along light path 24 to wavelength ratio scaling filter 18, which selectively filters, attenuates or decreases at least one of the desired wavelengths that were transmitted by wavelength selection filter 16. The emanating light then continues along light path 24 to eyepiece ocular 20, where the light can be viewed as an image by the eye or eyes of the user.

Figure 2:
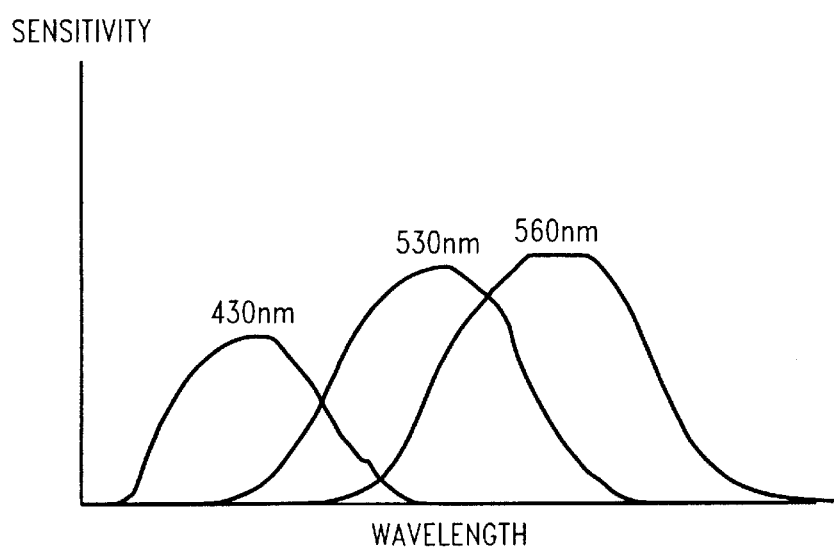
FIG. 2 is a graph describing the color response of the human eye.

FIG. 2 comprises a graph that depicts the spectral sensitivity curves, or color response, of the cones and rods that are found in the human eye. The wavelengths of maximum absorbance are indicated at the top of each curve. The 430 nm curve represents the absorbance spectrum for the short wavelengthsensitive cones of the eye, the 530 nm curve represents the absorbance spectrum for the rods of the eye, and the 560 nm wavelength curve represents the absorbance spectrum for the middle and long wavelength-sensitive cones of the eye.

Figure 3A:
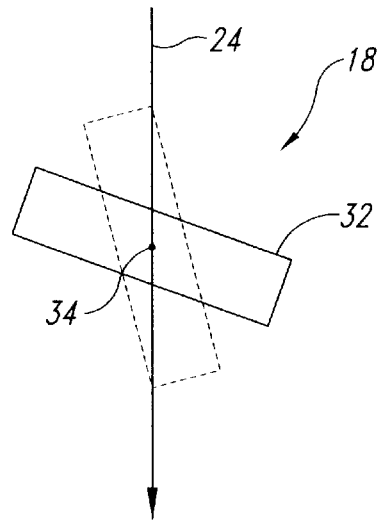
FIG. 3A is a side view of an embodiment of an emission wavelength ratio scaling filter wherein the filter is angularly adjustable.

FIG. 3A depicts one embodiment of an adjustable wavelength ratio scaling filter 18 wherein the filter is angularly or rotatably adjustable. Filter 32 is disposed in light path 24 such that when filter 32 is perpendicular to light path 24 filter 32 blocks about 50–90% of the selected desired wavelength band of light. Filter 32 can then be rotated about axis 34 such that light path 24 is transmitted through a greater amount of the filter (shown in broken line). As the amount of filter relative to light path 24 increases, the degree of blockage also increases, for example up to about 90–99% of the selected desired wavelength band.

Figure 3B:
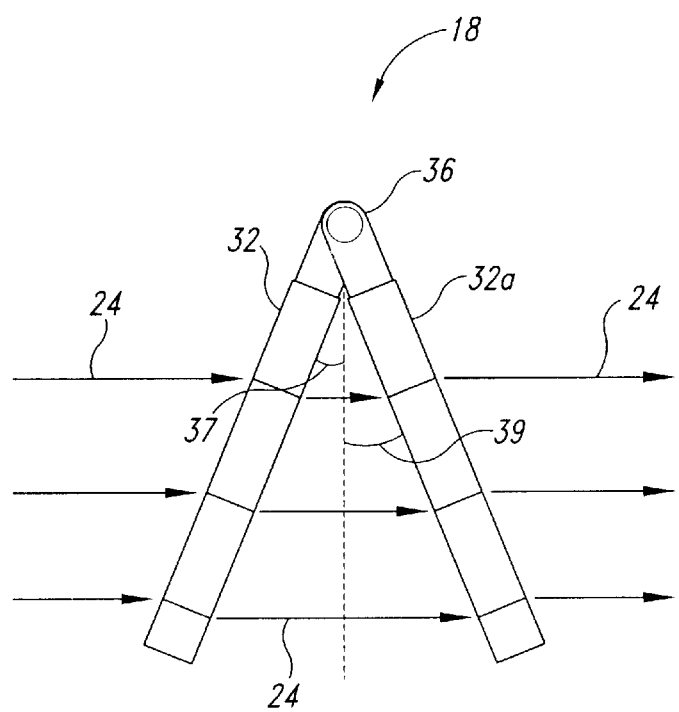
FIG. 3B is a schematic side view of an emission wavelength ratio scaling filter similar to that set forth in FIG. 3A, except that there are two filters that are angularly co-adjustable.

FIG. 3B depicts another embodiment of an angularly adjustable wavelength ratio scaling filter 18 comprising two filters 32 and 32a that are disposed in light path 24. The angle of each filter 32 or 32a is adjusted at a hinge 36 such that a first angle 37 between filter 32 and a line perpendicular to light path 24 is always equal to a corresponding second angle 39 between filter 32a and such perpendicular line.

Figure 3C:
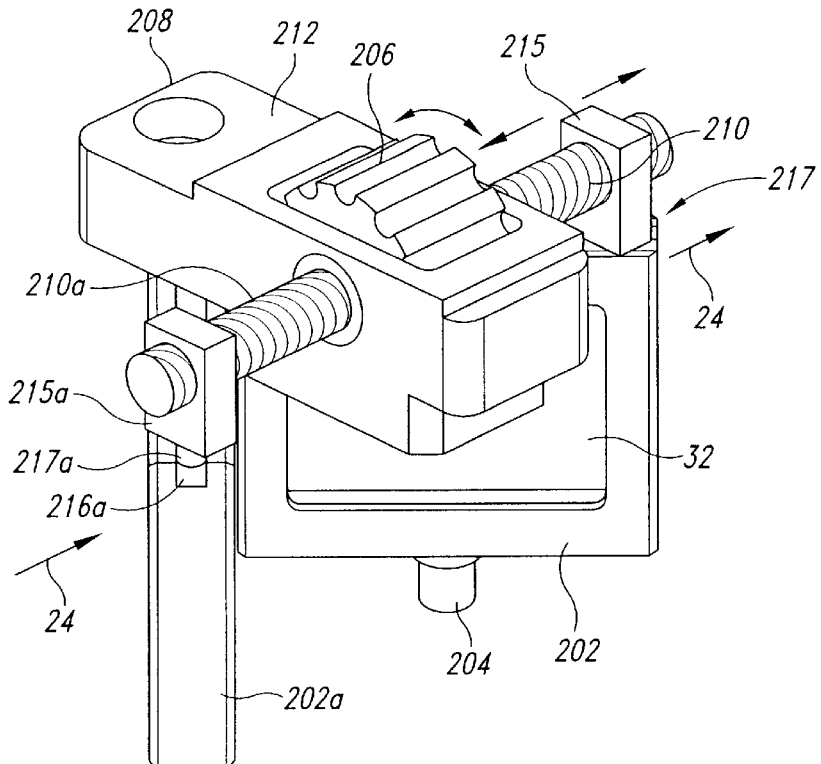
FIG. 3C is an isometric view of an emission wavelength ratio scaling filter similar to that set forth in FIG. 3B.
Figure 3D:
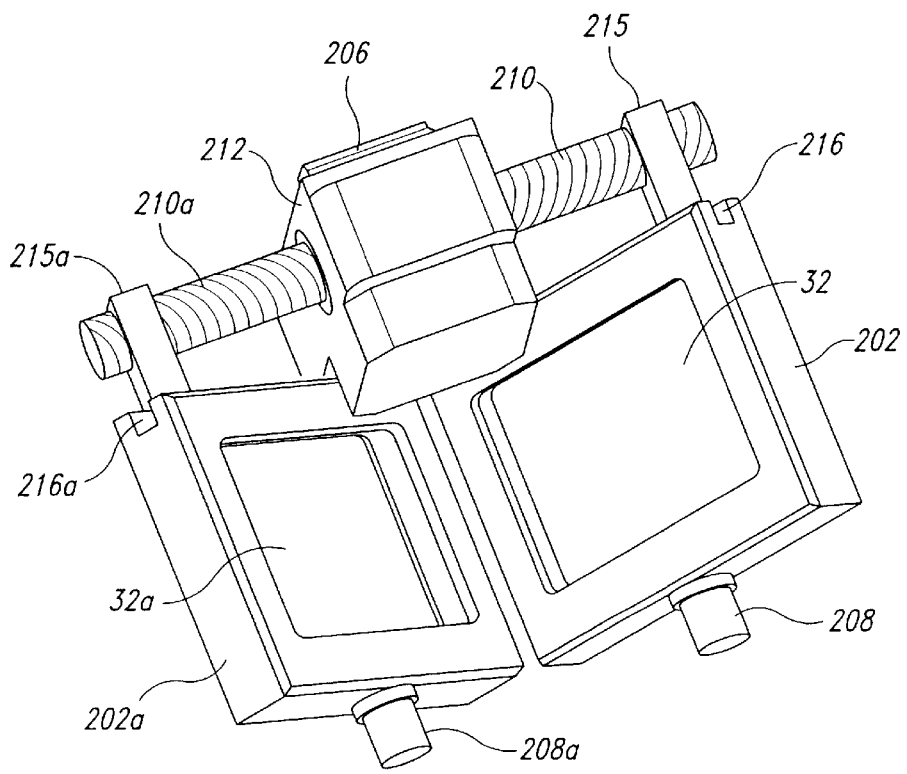
FIG. 3D is a second isometric view of the emission wavelength ratio scaling filter set forth in FIG. 3C.

FIGS. 3C and 3D depict a further embodiment of a co-angularly adjustable wavelength ratio scaling filter such as that depicted schematically in FIG. 3B. In FIGS. 3C and 3D, the two filters 32, 32a are retained in filter holders 202, 202a, which are substantially square (other geometric shapes can be used as desired). The filter holders 202, 202a each have a pivot pin 204, 204a on its inferior surface, which pivot pins are rotatably lodged in corresponding receiving holes in a case (such as in-line casing 220 depicted in FIGS. 3E and 3F). Filters 32, 32a simultaneously rotate through corresponding angular positions atop pivot pins 204, 204a when thumb wheel 206 is rotated by a user. Such rotation of thumb wheel 206 causes threaded projections 210, 210a to rotate within threaded filter supports 215, 215a, respectively. Each of threaded projections 210, 210a have corresponding, inverse threads such that rotation of thumb wheel 206 in a single direction causes threaded filter supports 215, 215a to simultaneously move outwardly or inwardly with respect to cross member support 212, depending upon the direction of rotation of thumb wheel 206. Filter holders 202, 202a each have a receiving channel 216, 216a in the superior surface thereof; such receiving channels receive nubs 217, 217a projecting from the inferior surface of threaded filter supports 215, 215a. Thus, as threaded filter supports 215, 215a are moved along threaded projections 210, 210a, their nubs 217, 217a move within receiving channels 216, 216a, thereby causing simultaneous, compensating rotation (i.e., co-angular movement) of filter holders 202, 202a and filters 32, 32a therein.

Figure 3E:
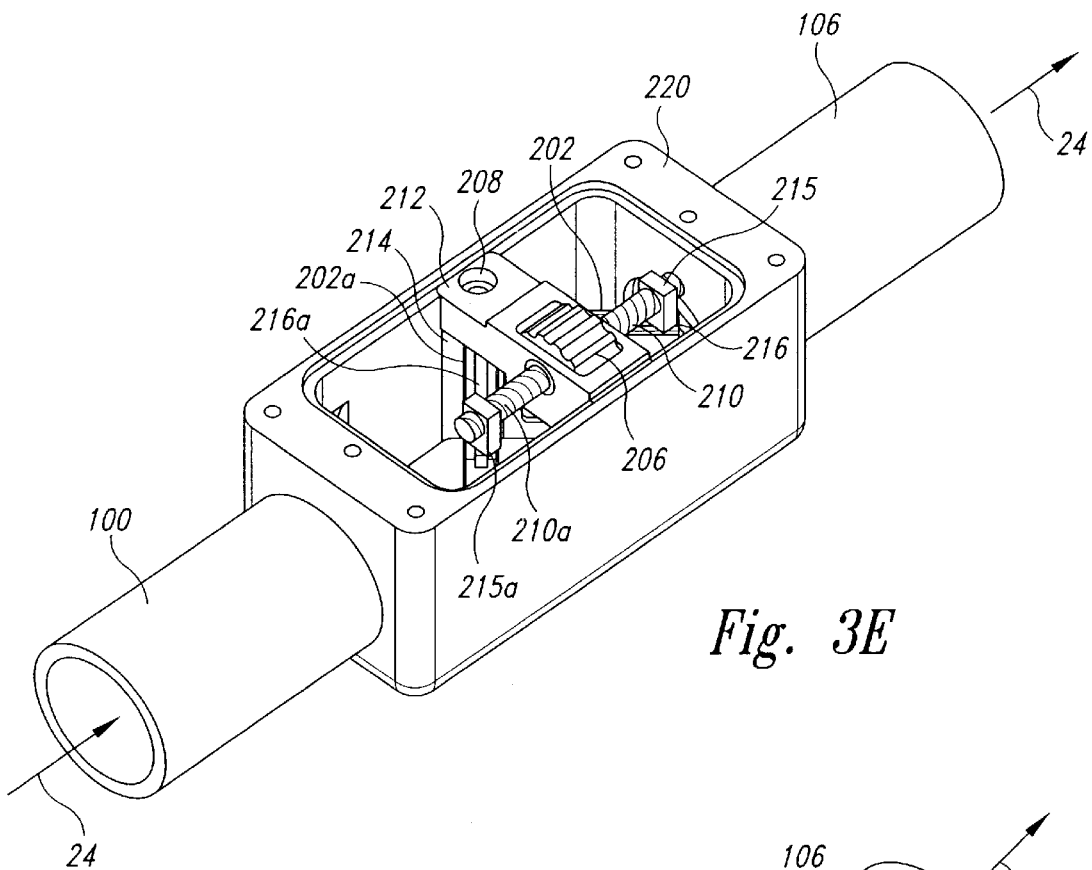
FIG. 3E is an isometric view of the emission wavelength ratio scaling filter set forth in FIGS. 3B and 3C, wherein the filter is disposed in-line in the body of an endoscope.
Figure 3F:
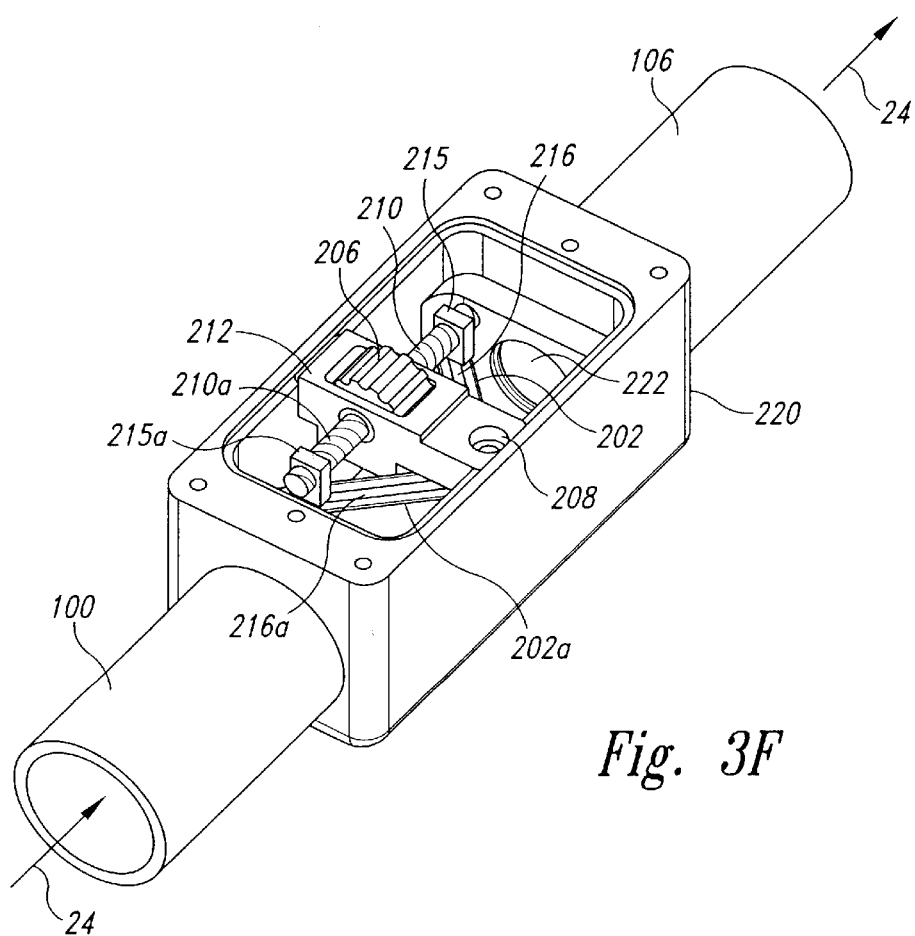
FIG. 3F is a second isometric view of the emission wavelength ratio scaling filter set forth in FIGS. 3B and 3C, wherein the filter is disposed in-line in the body of an endoscope.

Turning to FIGS. 3E and 3F, the co-angularly adjustable assembly of FIGS. 3C and 3D is depicted in place in an in-line casing 220 disposed within a distal sheath 100 and proximal sheath 106 of an endoscope. The coangularly adjustable assembly can be attached via a mounting screw that is transmitted through opening 208 in cross-member support 212 and into mounting screw receiving body 214 that is located within in-line casing 220. Preferably, in-line casing 220 comprises a lens 222 at its proximal end (a corresponding lens, not shown, is also preferably disposed in-line at the distal end of in-line casing 220), to maintain the clarity of the image transmitted by the endoscope.

Other methods and apparatus for co-adjusting the filters will be apparent to those of ordinary skill in the art in view of the present specification. By providing such co-adjusted filters, any deflection or other redirection of light path 24 upon passage through a first filter (e.g., filter 32) is corrected for by passage through the second filter (e.g., filter 32a).

Figure 3G:
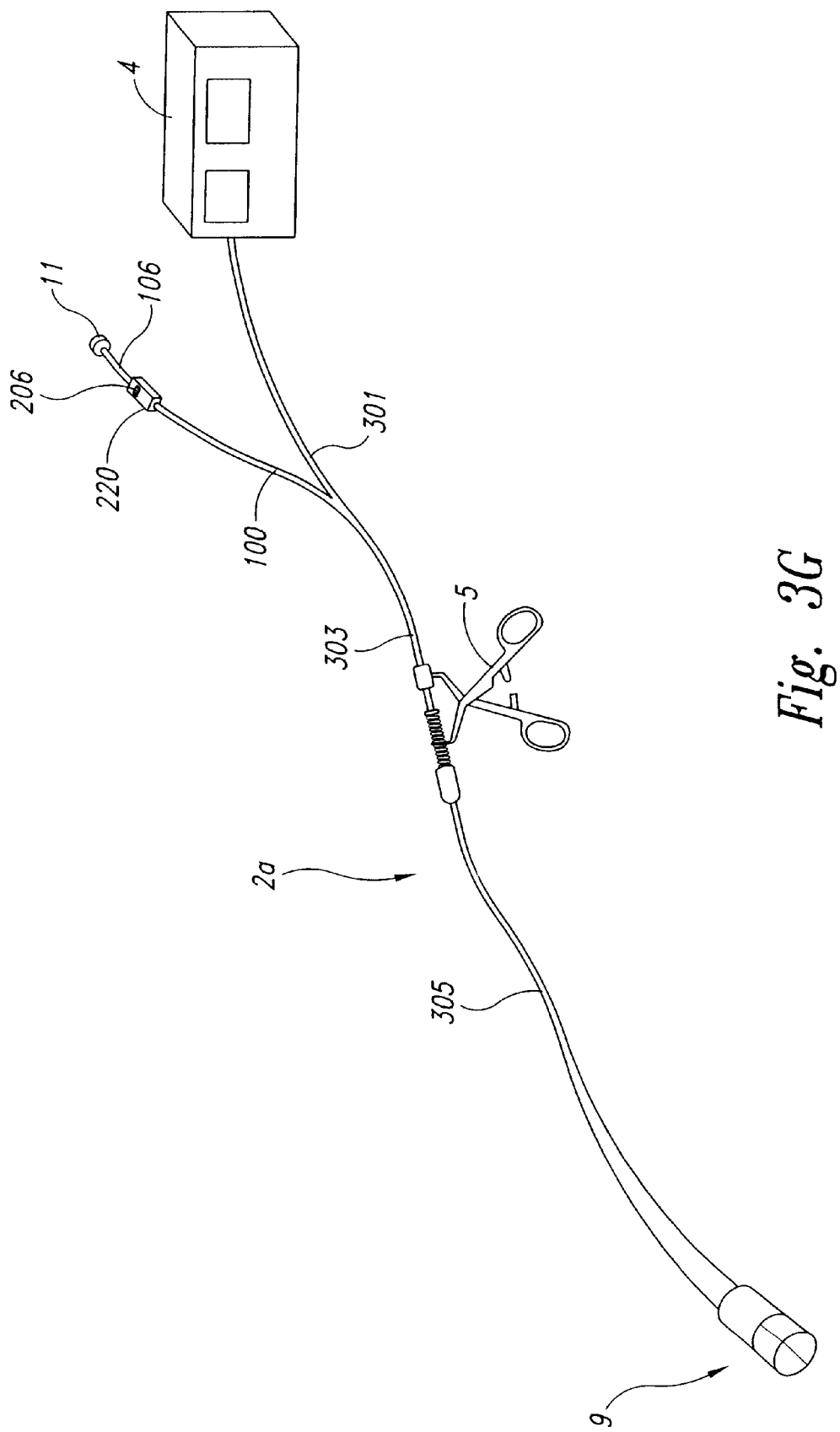
FIG. 3G is an isometric view of an optical bioptome in accordance with one embodiment of the invention including the wavelength ratio scaling filter shown in FIGS. 3B–3F.

FIG. 3G is an isometric view of an optical bioptome 2a with the in-line casing 220 housing the wavelength ratio scaling filter described above with reference to FIGS. 3B–3F. In this embodiment, the optical bioptome has a light source 4, a manipulator 5, a bioptome assembly 9, and an eyepiece 1. One suitable optical bioptome is disclosed in U.S. patent application Ser. No. 09/039,279, filed on Mar. 12, 1998, which is herein incorporated by reference as set forth above. As set forth above, the casing 220 is attached to a proximal sheath 106 and a distal sheath 100. The light source 4 is attached to an excitation sheath 301. The distal sheath 100 and the excitation sheath 301 join at proximal body section 303. The proximal end of manipulator 5 is attached to the proximal body section 303, and the distal end of the manipulator 5 is attached to a distal body section 305. The illumination light guide 7 (FIG. 1) is carried in the excitation sheath 301, proximal body section 303, and the distal body section 305. Similarly, the light collection system 22 is carried in the proximal and distal sheaths 106 and 100, and in the proximal and distal body sections 303 and 305. The bioptome assembly 9 is accordingly coupled to the illumination light guide 7 and the light collection system 22 at the distal end of the distal body section 305.

Figure 4A:
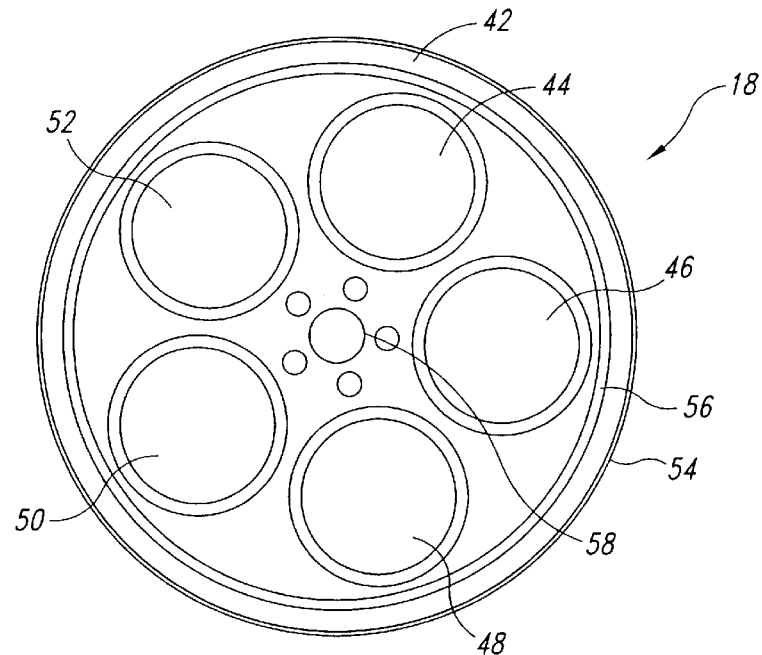
FIG. 4A is a top plan view of another embodiment of an emission wavelength ratio scaling filter, wherein the filter comprises multiple filters of different transmission levels set in a rotatable disk.

FIG. 4A depicts a further embodiment of an adjustable wavelength ratio scaling filter 18. The filter comprises a disk 42 comprising a plurality of openings disposed around a central aperture 58 sized to receive a supporting rod. Each of the openings contains a different filter for controlling the intensity of one or more selected desired wavelength band(s) (such as green light). For example, a first opening can contain a 60% filter 44 which blocks 60% of the selected desired wavelength band, while the second opening contains a 70% filter 46, the third opening contains an 80% filter 48, a fourth opening contains a 90% filter 50 and a fifth opening contains a 95% filter. In addition to blocking different amounts of the selected desired wavelength band (in this and other embodiments of the invention), the differing filters can also be selected to block different wavelength bands of light.

Figure 4B:
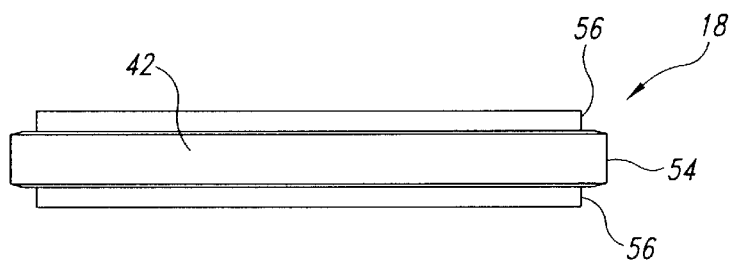
FIG. 4B is a side view of the emission wavelength ratio scaling filter depicted in FIG. 4A.
Figure 4C:
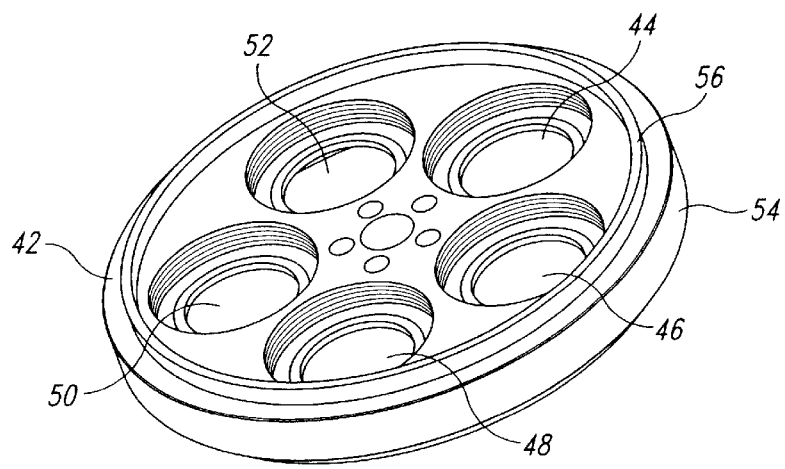
FIG. 4C is an isometric view of the emission wavelength ratio scaling filter depicted in FIG. 4A.

FIG. 4B is a side view and FIG. 4C is an isometric view of the wheel-type filter depicted in FIG. 4a. In FIG. 4b, a pair of spacing walls 56 are disposed on either side of the disk 42. The spacing walls 56 have a diameter that is less than the diameter of the outer edge 54 of the disk 42, and can be used to maintain spacing of the filters within the housing that contains the wheel-type filter depicted in the figure.

Figure 5:
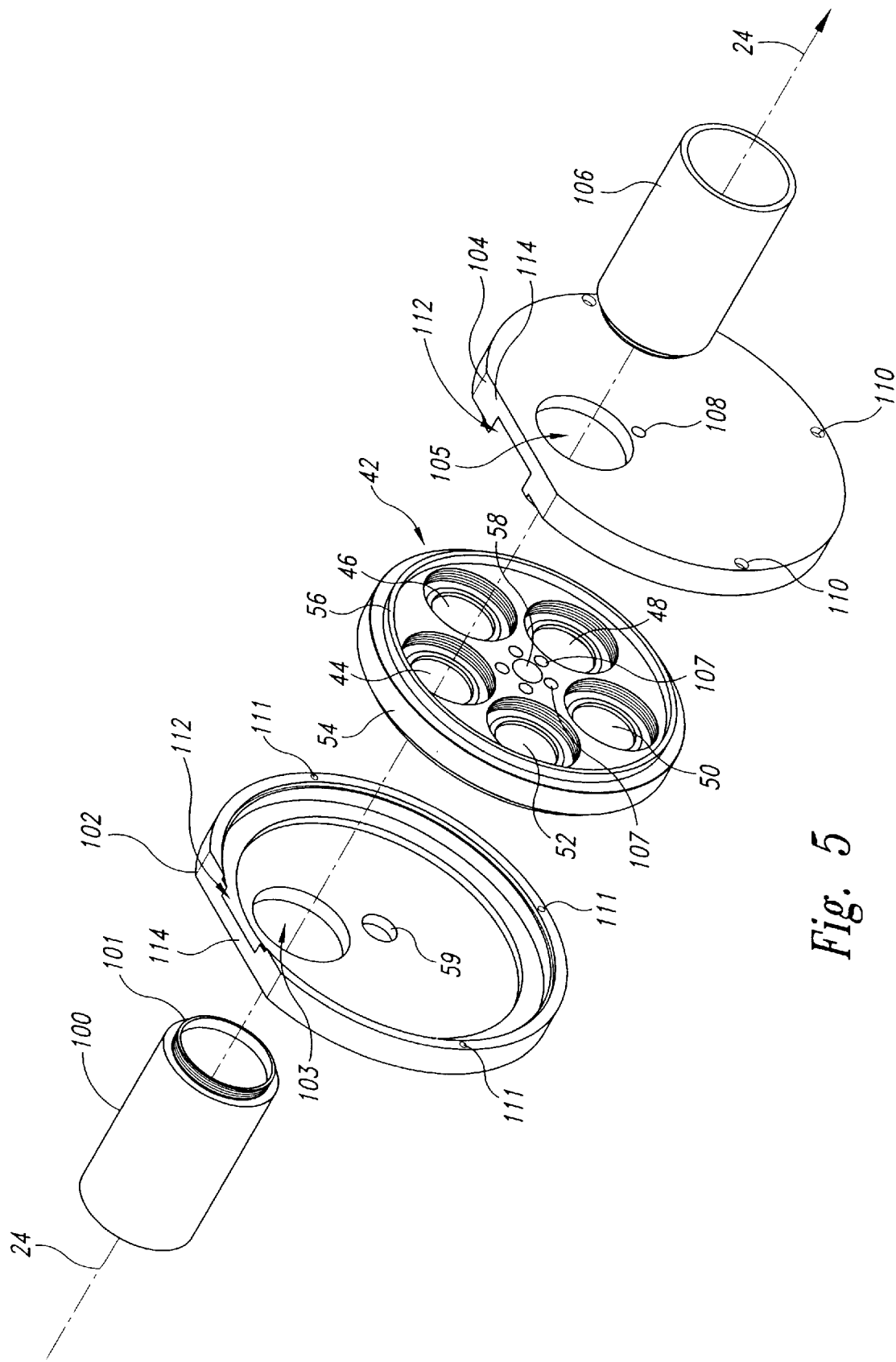
FIG. 5 is an exploded isometric view of the emission wavelength ratio scaling filter of FIGS. 4A–4C, wherein the filter is disposed in-line in the body of an endoscope.

FIG. 5 depicts an exploded isometric view of the wheel-type filter of FIGS. 4A–4C in position to be enclosed in a housing in the optical path of an in vivo optical viewer such as an endoscope. Disk 42 contains a central aperture 58 sized to receive a supporting rod (not shown) about which disk 42 can be rotated. Distal housing 102 contains a corresponding central aperture 59 for receiving the supporting rod. Referring to the assembly from distal end to proximal end, distal sheath 100 comprises a sheath of the in vivo optical viewer and communicates with the remainder of such viewer, typically including the distal end of the viewer. Distal sheath 100 comprises a lip 101 sized to be inserted into a light path opening 103 in distal housing 102 which housing is joined to proximal housing 104 having a corresponding light path opening 105, and which housing is joined to proximal sheath 106. Proximal sheath 106 then communicates with the eyepiece ocular for the eye(s) of the viewer. Distal housing 102 can be joined to proximal housing 104 via the use of screws or bolts (not shown) that are transmitted through holes 110 in proximal housing 104 and into threaded receptor holes 111 in distal housing 102. If desired, disk 42 can comprise a series of identifying marks 107 that identify the strength or other property of a corresponding filter. In preferred embodiments of the invention, as discussed above, specific markings indicate preferred filters for specific disease(s). Such identifying marks can be viewed through opening 108 in proximal housing 104. Alternatively, outer edge 54 of disk 42 can have identifying marks thereon, which can be seen because outer edge 54 extends through a space created by rectangular openings 112 in flattened surfaces 114 of each of distal housing 102 and proximal housing 104.

Figure 6:
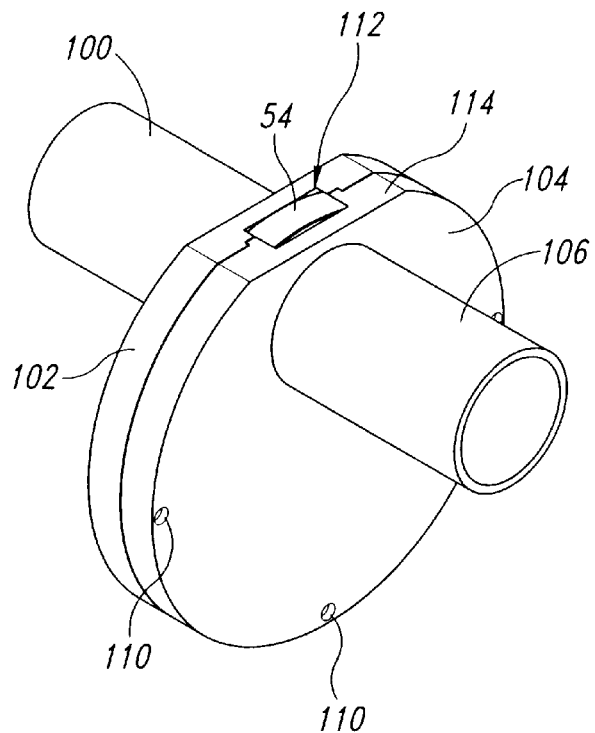
FIG. 6 is an isometric view of the emission wavelength ratio scaling filter of FIGS. 4A–5 enclosed in an in-line housing in an endoscope according to an embodiment of the present invention.

FIG. 6 depicts an isometric view of the assembly of FIG. 5 wherein the assembly has been put together. As can be seen, outer edge 54 of disk 42 is available for manipulation by a user, thereby permitting such user to easily turn disk 42 and place a desired filter in light path 24.

Figure 7:
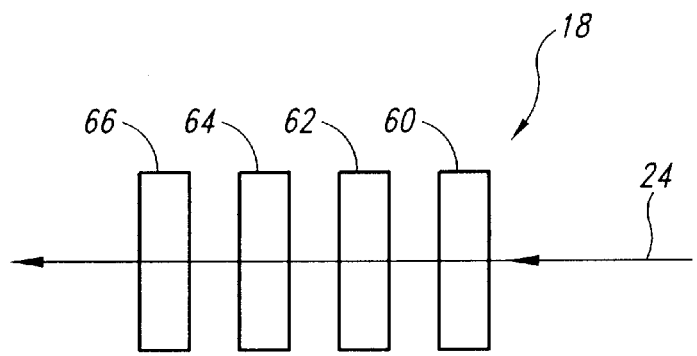
FIG. 7 is a side view of a further embodiment of an emission wavelength ratio scaling filter, wherein various strength filters are cascaded to be selectively interposed in a light path.

FIG. 7 is a schematic view illustrating a third embodiment of an adjustable wavelength ratio scaling filter wherein the filters are cascaded. In the figure, light path 24 traverses one or more filters disposed in a line and selectively interspersed into light path 24 to provide a variety of different levels of filtering. For example, in FIG. 7, the first filter is a 50% filter 60 that blocks 50% of the selected desired wavelength band, the second filter is a 20% filter 62 that blocks 20% of such light, the third filter is a 10% filter 64 and the fourth filter is a 5% filter 66. These filters can then be interspersed in the light path 24 either singly, all at once or in any desired combination to provide a variety of different levels of filtering. Of course, more or less than four filters can be used at the desire of the user.

Figure 8:
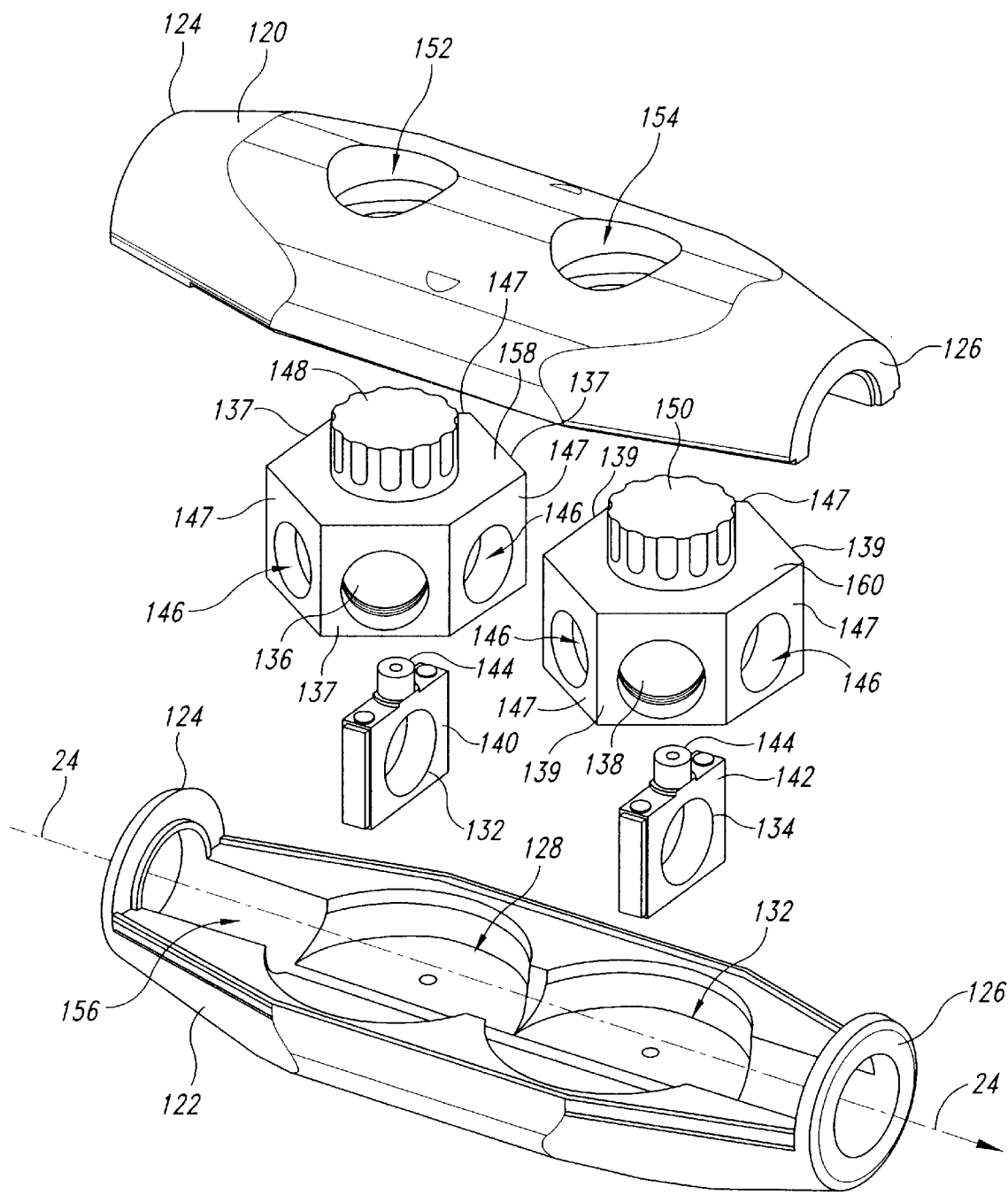
FIG. 8 is an exploded isometric view of one embodiment of an emission wavelength ratio scaling filter as depicted in FIG. 7, wherein the varying strength filters are retained in rotatable wheels.

FIG. 8 is an exploded isometric view illustrating a preferred embodiment of a filter assembly suitable for use with an adjustable wavelength ratio scaling filter having cascaded filters as in FIG. 7, wherein the filters are maintained in the sides of a rotatable, substantially circular housing that forms a part of the assembly. In FIG. 8, a lower casing 122 has a transmission passage 156 therein that is sized to receive and transmit light path 24. In addition, transmission passage 156 comprises a first chamber 128 and second chamber 130 that are each sized to receive first and second rotatable housings 158, 160, respectively. The rotatable housings 158, 160 are substantially cylindrical, and can be hexagonal or otherwise geometrically shaped, such as other polygons, circles or ovals in cross-section.

Each of the rotatable housings 158, 160 contains therein a plurality of different filters 136, 138 and a corresponding plurality of openings 146 disposed in the opposite wall of the housings relative to the filter. For example, the rotatable housing 158 has a first filter 136 on alternating sides 137, and holes 146 on alternating sides 147. Similarly, rotatable housing 160 has a second filter 138 on alternating sides 137, and holes 146 on alternating sides 147. In other embodiments, adjacent faces on one-half of the housings 158 or 160 have a series of filters, and opposing adjacent faces on an opposing half of the housings have holes. The filters and holes in the housings 158 or 160 can be configured in still other arrangements such that filters are positioned across from one another on opposite sides of the same housing.

Each of the housings 158, 160 also has knobs 148, 150 projecting from the superior surface thereof and that permit a user to rotate the housings 158, 160 when they are enclosed within lower casing 122 and upper casing 120. By rotating either knob 148 and/or knob 150, a user is able to place one of the plurality of filters maintained within each housing in light path 24. The corresponding opening 146 in the housing permits the light to continue downstream along light path 24. Each of the housings, casings, knobs, and other parts of this filter assembly can be formed, sculpted, molded or otherwise manufactured from any desirable material, such as plastic or metal.

Preferably, the filter assembly further comprises a first lens 132 and a second lens 134 disposed in first lens holder 140 and second lens holder 142, each of which can be supported by a swivel attachment 144 to the remainder of the assembly. The first lens holder 140 is positioned within the housing 158, and the second lens holder 142 is positioned within the housing 160. Thus, the lenses are disposed, preferably perpendicularly, within light path 24 and serve to maintain or enhance the sharpness of the image transmitted along light path 24. Additionally, because of their swivel mounting within the assembly relative to rotatable housings 158, 160, the lens holders 140 and 142 (and therefore the lenses 132, 134 carried therein) do not rotate relative to light path 24 when knobs 148, 150 are turned. In an alternative format, lens holders 140, 142 can attached to lower casing 122 and do not physically contact rotatable casings 158, 160, thereby avoiding any possibility of being rotated due to the rotation of such casings. The system can be used without filters if desired.

Upon closure of the upper casing 120 with lower casing 122, control knobs 148, 150 can be manipulated through first receiving hole 152 and second receiving hole 154. Preferably, the control knobs extend well beyond receiving holes 152, 154 for ease of manipulation. Thus, light traveling upon light path 24 enters the distal end 124 of the casing, passes through one of the first filters 136 on a side 137 of the first housing 158 facing the distal end (which filter has been rotated to be in line within light path 124), then the light traverses first lens 132, passes through a first opening 146 in the first rotatable housing 158 facing the proximal end 126, traverses one of the second filters 138 on side 139 of the second rotatable housing 160 facing the distal end 124 (which has also been rotated to be in line within light path 24), then traverses second lens 134, passes through a second opening 146 in the second rotatable housing 160 facing the proximal end 126, and then continues downstream to exit the assembly at proximal the end 126.

In other embodiments, the assembly can comprise only one or more of the rotatable housings (e.g., 3). Additionally, each rotatable housing can comprise three filters and three corresponding openings as described in the figure, or such housings can comprise any desirable number of filters and corresponding openings, provided that the diameter of a cross section of light path 24 does not impinge upon a plurality of filters in a single casing due to the filters having been made to small. In addition, a single opening can be used to provide a passageway for light traversing more than one filter by sizing the opening large enough to encompass the area covered by the filters. Indeed, the housing can even be substantially semi-cylindrical, with filters embedded within the wall formed by the semi-housing and the open "half" of the housing being equivalent to the openings 146 in FIG. 8.

The apparatus and methods of the present invention are typically used, and the methods are typically performed, on living animals, preferably human patients. The apparatus and methods can also be used post-mortem, if desired. Thus, the illumination light is transmitted and the fluorescence, or other return light, is collected in vivo.

Turning to some alternative embodiments of the invention, in one such embodiment the emanating light from the target tissue can be directed into an optical beam splitter that divides the light into two or more beams and/or spectral regions of interest. The multiple beams and/or spectrally separated components are then each directed to discrete viewers, such as the different lenses of a binocular viewer.

In another embodiment of the invention, where the in vivo optical viewer is an endoscope, the distal end of the endoscope comprises a bioptome, which bioptome is preferably extensible and retractable. See U.S. patent application Ser. No. 09/039,279, filed Mar. 12, 1998 and entitled Catheters And Endoscopes Comprising Optical Probes And Bioptomes And Methods Of Using The Same, and the references cited therein. A bioptome is a device that snips off a piece of a target tissue for extraction from an organism and evaluation. Bioptomes typically comprise a pair of opposing jaws, but other configurations are also known. U.S. Pat. No. 3,964,468; U.S. Pat. No. 4,953,559; U.S. Pat. No. 4,884,567; U.S. Pat. No. 5,287,857; U.S. Pat. No. 5,406,959;

WO 96/35374; WO 96/35382; WO 96/29936; WO 96/35374. Inclusion of a bioptome allows a surgeon to both select optical scanning sites and perform tissue biopsy, and thus allows simple and easy biopsy with minimal risk and reduced harm to the patient because of shortened overall surgical procedure time and fewer insertions of endoscopes into the body. These advantages are achieved because fewer tissue biopsies should be necessary because no biopsy will be taken when the optical review shows that there is no need for biopsy, and because the combination of the bioptome with the optical probe permits optical viewing and biopsy without removal of the endoscope carrying the optical bioptome.

In another aspect of the invention, a liquid-carrying lumen that allows a bolus of non-fluorescing, non-reflecting liquid saline solution to be pumped to the distal tip of the endoscope is co-luminal with the light guides. The structure of the endoscope tip directs the liquid around the optical fibers and out to the tissue so that the resultant jet of liquid pushes aside blood or other interfering material and acts as a liquid light path for transmission of light to, and collection of light from, the target tissue.

In a further aspect of the invention, the distal tip of the optical probe or endoscope is covered with and bonded to an elastomeric balloon comprising an optically transmissive window that is preferably non-fluorescing and non-reflective. Upon opening of the jaws and extension of the light probe, a bolus of gas or liquid is pumped into the balloon to cause it to distend and thereby contact the window with the tissue. The liquid or gas, which can be air, in the balloon acts as an optically clear path to the tissue, while the balloon pushes blood and other interfering material out of the field of view.

The following discussion sets forth some non-limiting examples of components that are advantageous for use with the methods and apparatus of the present invention.

Light Sources

The present invention can use any light source that provides a light that illuminates a target tissue. In one preferred embodiment, the illumination light induces fluorescence in the target tissue. For some aspects of the invention, the light source need not induce fluorescence, but may instead cause reflectance or other light to return from the target tissue. Selection of an appropriate light source is well within the ordinary skill in the art in view of the present specification. With regard to light sources that induce fluorescence, the light source can be selected to provide light from ultraviolet (UV) through visible light. Preferably, the light comprises green, blue or near-UV light. Also preferably, the light does not comprise UV light because such light can induce cancer or other problems within the patient organism, which is preferably a human being. Further preferably, the light consists essentially of blue light and/or green light.

Some examples of preferred light sources to generate the required excitation energy include a pulsed xenon flashlamp equipped with wavelength selection filters (FIG. 10), a CW (continuous wave) mercury or xenon arc lamp equipped with wavelength selection filters (FIGS. 11 and 12), a Blue or UV CW laser, and a Blue or UV pulsed laser. These are discussed below. The light sources in these figures preferably have an indexed mechanical coupling adapter 82 moveably attached to an optically transmissive base 80 to move a waveguide 84 transverse with respect to a light path 24. The indexed mechanical coupling adapter ensures that the illumination waveguide 84 is positioned to maximize the amount of light entering the illumination waveguide 84, and can be controlled by system software, which controls pulse timing of the arc lamp power supply. Suitable indexed mechanical coupling adapters 82 are known in the art.

Figure 10:
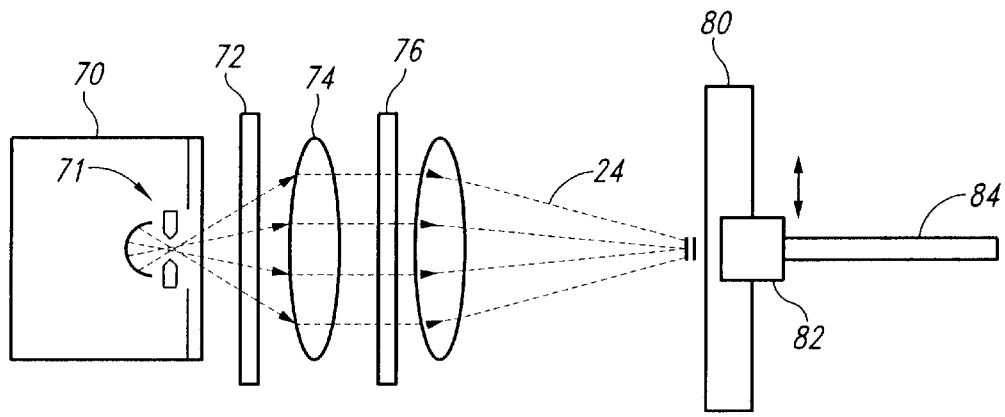
FIG. 10 is a schematic drawing of a pulsed xenon flashlamp source.

In FIG. 10, a pulsed xenon flashlamp 70 comprises a sealed housing arc lamp 71 and power supply (not shown). The arc lamp 71 typically has an arc length of less than 2 mm and is optionally equipped with an integral reflector to maximize energy directed toward the illumination light guide of the endoscope, catheter or other optical probe. An optical filter or series of filters, such as a blocking filter 72 and wavelength selection filter 76 placed in the optical path, can select the wavelength of the illumination light. The energy emitted by the arc lamp is collected and focused by a focusing lens 78. A collimating lens 74 can be placed between the filters if desired to direct the light from the arc lamp 71 along a common path. In a preferred embodiment suitable for use with the present invention, the lenses 74 and 78 are selected to direct the energy in a converging cone into the illumination light guide 84, with an apex angle that is less than or equal to the acceptance angle of the illumination light guide as defined by the numerical aperture of the illumination light guide.

Figure 11:
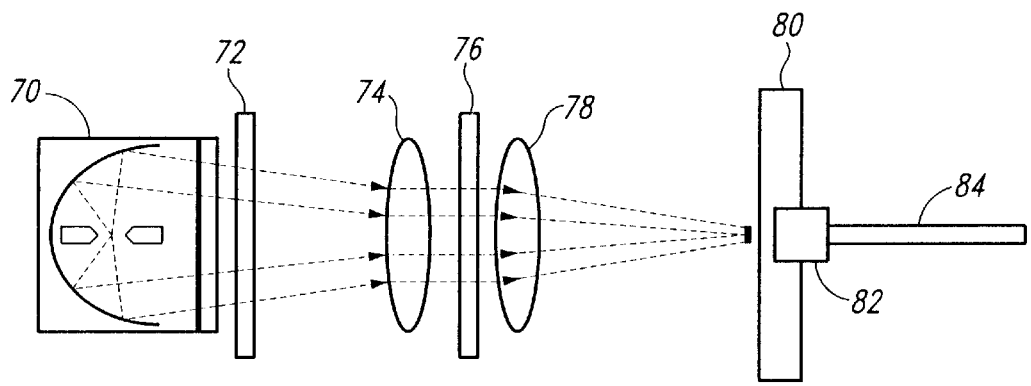
FIG. 11 is a schematic drawing of a focused continuous wave (CW) arc lamp.
Figure 12:
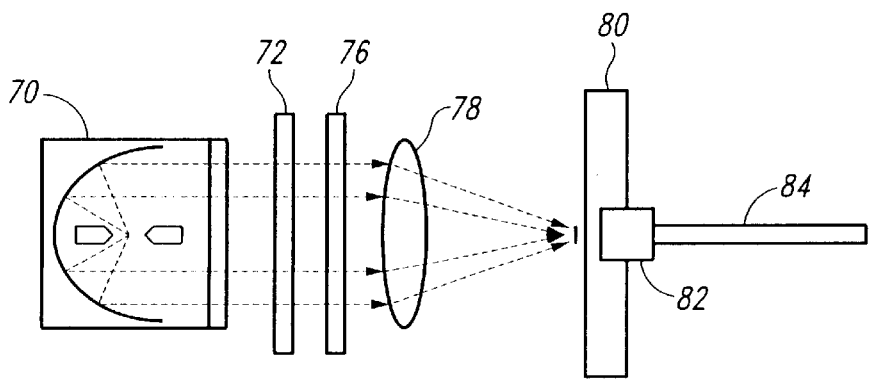
FIG. 12 is a schematic drawing of a collimated CW arc lamp.

In FIGS. 11 and 12, a CW mercury or xenon arc lamp light source, respectively comprises a sealed housing arc lamp 90 and power supply (not shown). The arc lamp typically has an arc length of less than 2 mm and is optionally equipped with an integral or external reflector to maximize energy directed toward the illumination waveguide of the catheter or optical probe. An optical filter or series of filters (e.g., the blocking filter 72 and/or the wavelength selection filter 76) placed in the optical path can select the wavelength of the illumination light. The energy emitted by the arc lamp is collected and focused by a lens system (e.g., the focusing lines 78 with or without the collimating lens 74). The lenses are selected to direct the energy into the illumination light guide in a converging cone with an apex angle that is less than or equal to the acceptance angle defined by the numerical aperture of the illumination light guide. In one embodiment, the lamp power supply operates continuously with no pulsing. Alternatively, the lamp can be powered by a sinusoidally varying current/voltage, which can also enhance the blue wavelength emission of the lamp. In other embodiments, the source of electromagnetic energy can be a laser.

A blue or UV CW laser light source comprises a laser that emits light in the blue or near ultraviolet wavelengths. Wavelength selection can be accomplished by using a laser such as a Helium-Cadmium (HeCd) laser or a Krypton-Argon laser that emits light in the blue portion of the spectrum. Alternatively, a dye laser pumped by a shorter wavelength laser wherein wavelength selection is a function of dye characteristics and cavity monochrometer tuning can be used. The energy emitted by the laser is collected and focused by a lens system. The lenses are selected to direct the energy into the illumination light guide in a converging cone with an apex angle that is less than or equal to the acceptance angle defined by the numerical aperture of the illumination light guide. The laser can be equipped with a manual and/or computer controlled shutter. Suitable CW laser light sources and lens systems are known in the art.

Another type of suitable laser is a blue or UV pulsed laser light source that comprises a laser that emits light in the blue or near ultraviolet wavelengths. The pulse laser emits short duration pulses, preferably under software program control. Wavelength selection can be accomplished by using a dye laser pumped by a shorter wavelength laser wherein wavelength selection is a function of dye characteristics and cavity monochrometer tuning. Alternatively, a longer wavelength laser equipped with a frequency doubling system and/or an optical parametric oscillator (OPO) can be used. The energy emitted by the laser is collected and focused by a lens system. The lenses are selected to direct the energy into the illumination light guide in a converging cone with an apex angle that is less than or equal to the acceptance angle defined by the numerical aperture of the illumination light guide.

Figure 13:
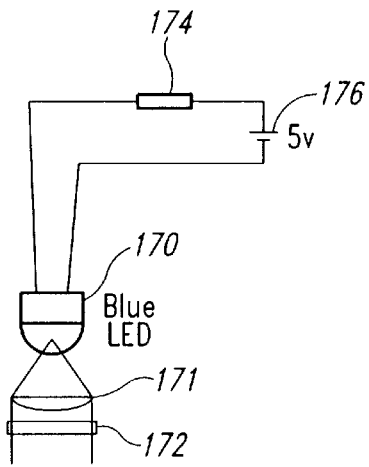
FIG. 13 is a schematic diagram depicting an embodiment of the present invention comprising a system for inducing fluorescence wherein an LED is disposed at the distal end of an endoscope.
Figure 14:
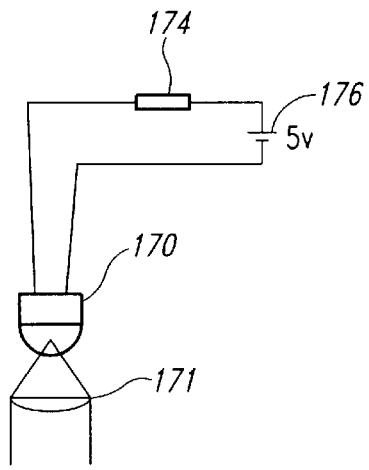
FIG. 14 is a schematic diagram depicting another embodiment of the present invention comprising an illumination apparatus wherein an LED is disposed at the distal end of an optical viewer.

Turning to another embodiment, FIG. 13 is a schematic diagram showing a system wherein the light is emitted by a distally-located blue LED 170, which light is collimated by a collimating microlens 171 and then filtered by a short pass filter 172 to transmit the illumination to the skin for fluorescence excitation. FIG. 14 is a schematic diagram showing light from a distally-located LED that can be other than a blue LED, and thus lacking short pass filter 172 which could be incompatible with the light emitted by a given LED (of course, other filters, such as long pass filters or band pass filters, can be placed in the position of short pass filter 172 if desired). Multiple LEDs can be used in order to increase the illumination power and/or provide multiple wavelengths of illumination light. Thus, a blue LED, a green LED, and a red LED can be used to provide full spectral illumination for reflectance measurements or other desired measurements, such as Raman responses.

Figure 15:
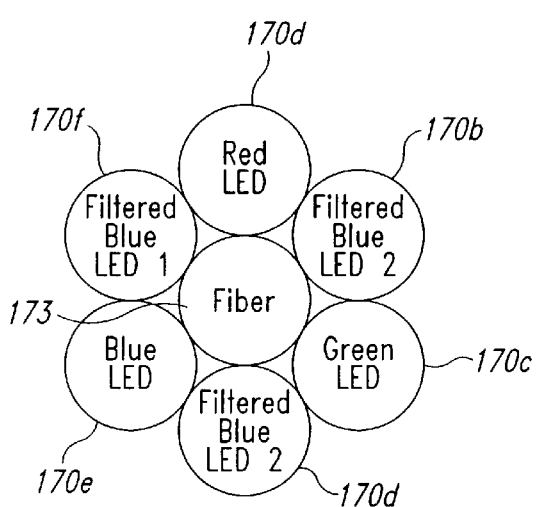
FIG. 15 is an and end view of an array of illumination LEDs disposed around a collection light guide.
Figure 16:
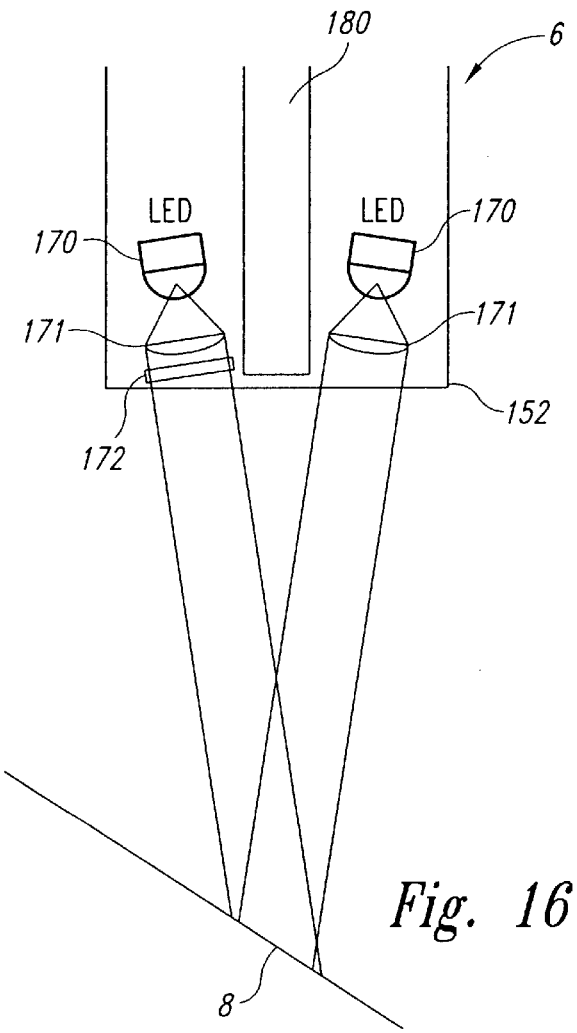
FIG. 16 is a schematic diagram depicting a side view of an array as set forth in FIG. 15.

FIG. 15 shows one desired arrangement of the LEDs 170 (specifically identified by reference numbers 170a–170f) relative to the collection fiber 173 wherein the LEDs are located at the distal end of a probe. FIG. 16 is a schematic diagram showing an LED assembly wherein the LEDs 170 are slightly tilted toward each other and a collection fiber 80 at the distal end 52 of an optical probe 6 and co-centered at a central point of a potential skin disease site 8. This arrangement enhances the ability of the LEDs to illuminate the same area of potential skin disease site 8.

Light Filters

The present invention can use any light filter that provides the selection and attenuation of light discussed herein. The making of such filters can be done using methods well known in the art and can be obtained, provided the desired requirements are set forth, for example, from Melles-Griot, Irvine, Calif.; Ealing Electro-Optical, Inc., Holliston, Md.; Corion, Brattleboro, N.H. Alternatively, the filters can be custom made according to the desires of the user.

Figure 17A:
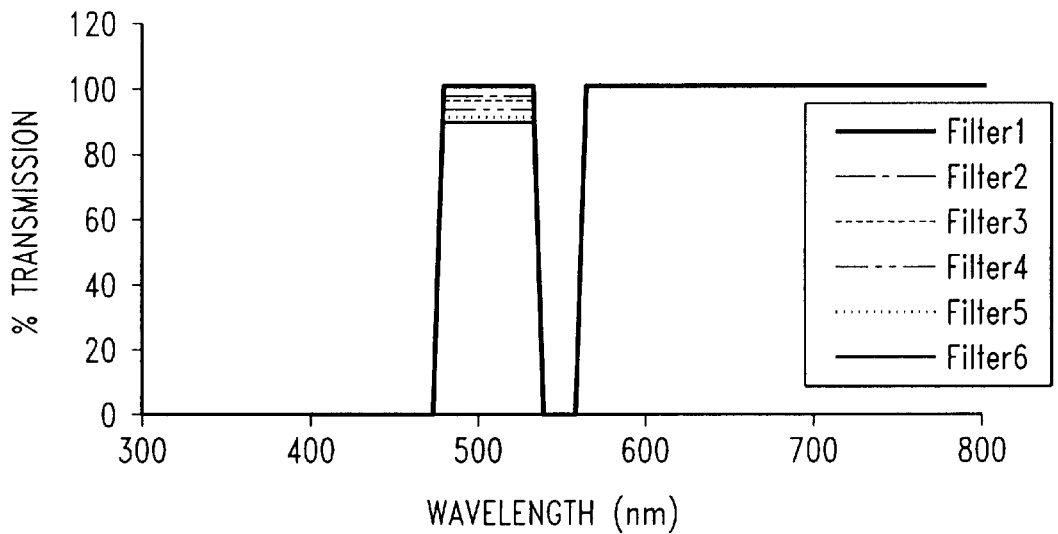
FIGS. 17A–17C are graphs depicting the percent transmission of a red-green wavelength selection filter, a red-green wavelength ratio scaling filter having six discrete filters, and a red-green wavelength ratio scaling filter wherein the filtration of the red-green wavelength is continuously variable as a function of angle (with six selected angles isolated and depicted), respectively, according to one embodiment of the present invention.
Figure 17B:
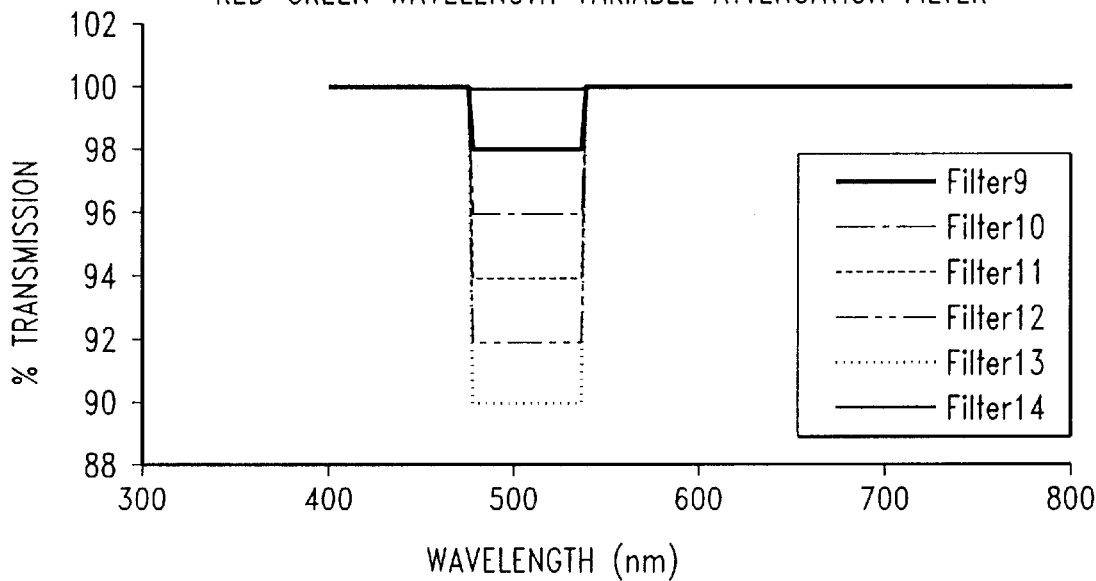
Figure 17C:
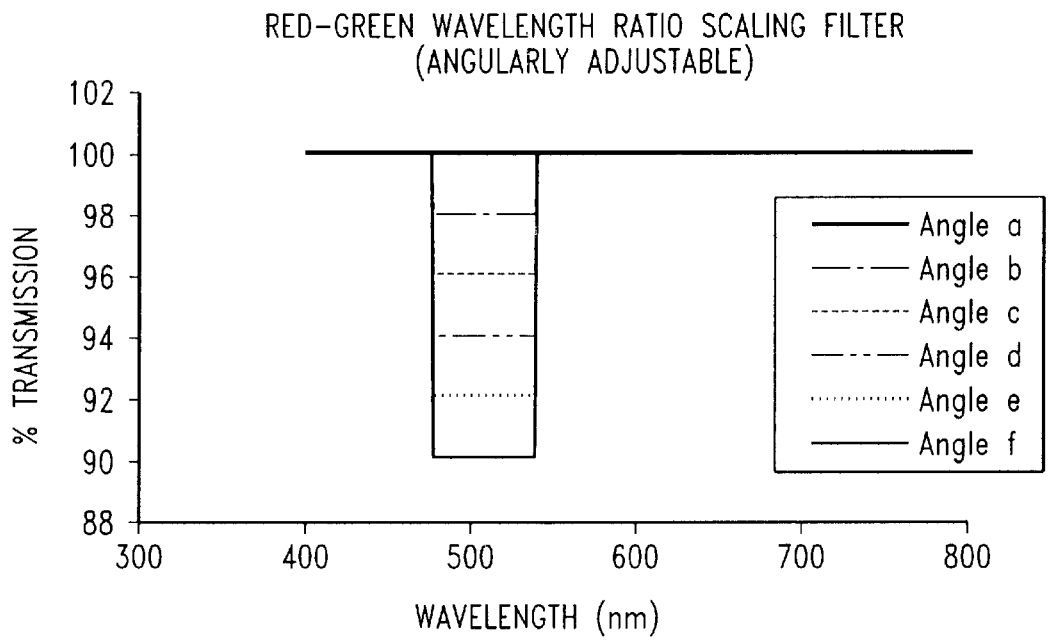

Examples of wavelengths filtered or transmitted by suitable light filters are set forth in FIGS. 17A–17C and 18A–18C. FIG. 17A depicts a graph showing the percent transmission of a red-green wavelength selection filter. The filter transmits light in the red and green wavelengths, and can include some attenuation of one or the other of the wavelength bands (green in FIG. 17A). Typically, such attenuation is not effectuated in the wavelength selection filter, but rather solely in the wavelength ratio scaling filter. FIGS. 17B and 17C depict graphs showing attenuation the green light transmitted by the wavelength selection filter in FIG. 17A, shown as the percent transmission of the green light. FIG. 17B shows the level of attenuation in correlation to a series of discrete, different strength filters such as those set forth in FIGS. 4–8, while FIG. 17C shows the level of attenuation in correlation to a series of different angles of an angularly adjustable filter such as those set forth in FIGS. 3A–3F (with six selected angles isolated and depicted).

Figure 18A:
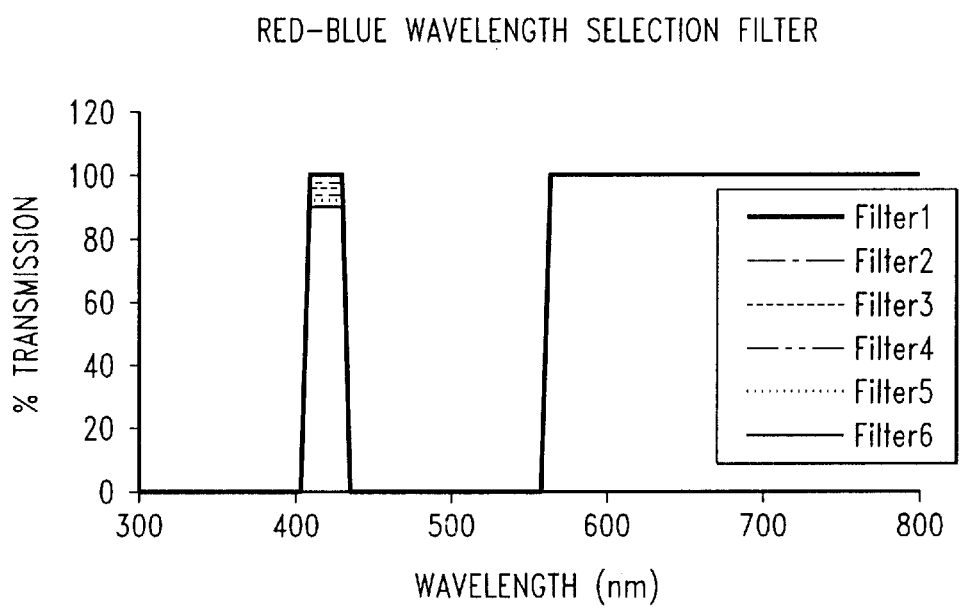
FIGS. 18A–18C are graphs depicting the percent transmission of a red-blue wavelength selection filter, a red-blue wavelength ratio scaling filter having six discrete filters and a red-blue wavelength ratio scaling filter wherein the filtration of the red-blue wavelength is continuously variable as a function of angle (with six selected angles isolated and depicted), respectively, according to one embodiment of the present invention.
Figure 18B:
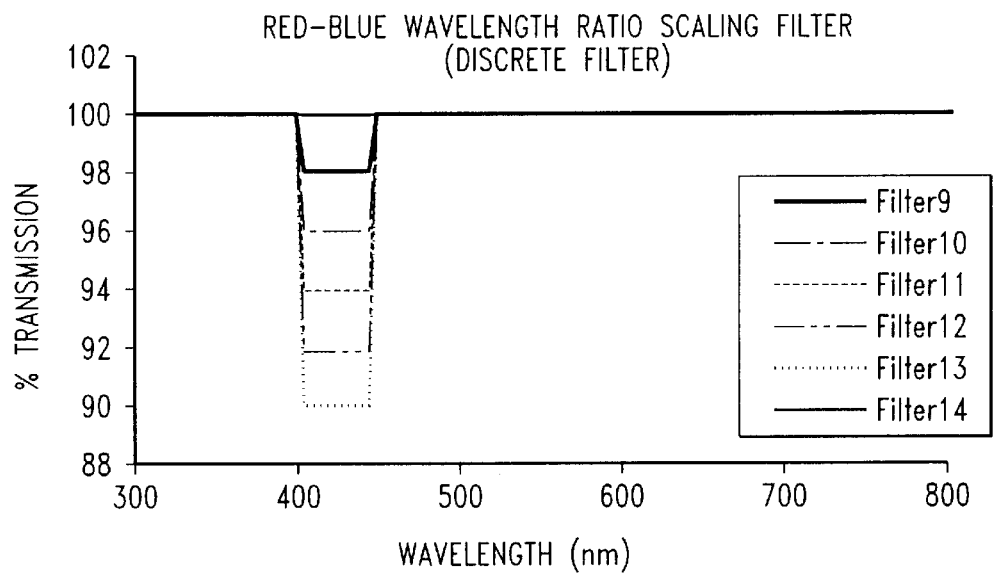
Figure 18C:
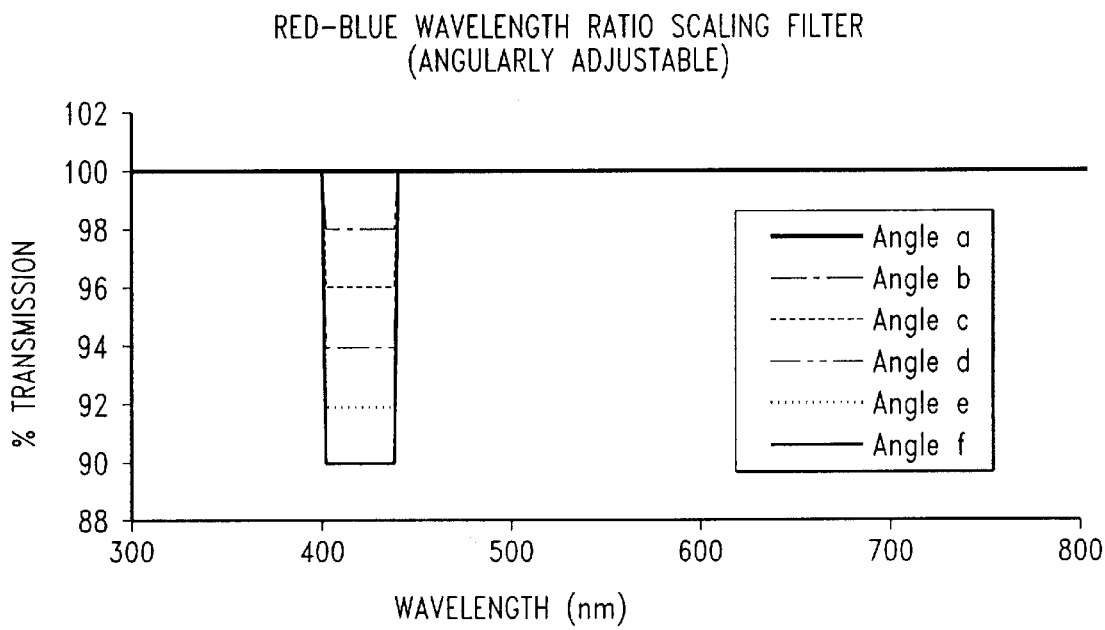

FIGS. 18A–18C correspond to FIGS. 17A–17C, respectively, except that they depict the selection and attenuation that is attained with a redblue wavelength selection filter, a red-blue wavelength ratio scaling filter having six discrete filters and a red-blue wavelength ratio scaling filter wherein the filtration of the red-blue wavelength is continuously variable as a function of angle (with six selected angles isolated and depicted), respectively.

What is claimed is:

1. An endoscope for directly transmitting an image from an in vivo target tissue to a user, the endoscope comprising:

a body including a proximal end and a distal end, the body being configured to position the distal end proximate to the target tissue;

a light emitter proximate to the distal end to direct an illumination light to the target tissue;

an eyepiece ocular coupled to the body at the proximal end that is sized to fit a human eye;

at least one collection light guide including a collector to receive emanating light from the target tissue and a conductor to conduct the emanating light along at least a portion of a light path to the eyepiece ocular which transmits the emanating light to the eye to form a light collection system, wherein the user is able to directly view the target tissue directly through the eyepiece ocular without a transduction imaging device between the target tissue and the user;

a wavelength selection filter aligned with the collection light guide to be disposed in the light path, the wavelength selection filter selectively transmitting at least two desired wavelength bands of the emanating light; and a wavelength ratio scaling filter aligned with the collection light guide to be disposed in the light path, the wavelength ratio scaling filter selectively controlling the intensity of at least one of the desired wavelength bands, the wavelength selection filter and the wavelength ratio scaling filter manipulating the emanating light from the target tissue to selectively enhance an image of the target tissue;

wherein the illumination light transmitted to the target tissue consists essentially of a selected wavelength band and the light collection system further comprises a long pass filter disposed in the light path, wherein the long pass filter blocks light having about the same wavelength as the selected wavelength band and transmits other light.

2. The endoscope of claim 1 wherein the long pass filter is disposed at the distal end of the light collection system.

3. The endoscope of claim 2 wherein the long pass filter is maintained upstream from the collection light guide which is maintained upstream from the wavelength selection filter which is maintained upstream from the wavelength ratio scaling filter.

4. The endoscope of claim 1 wherein the long pass filter blocks blue light.

5. The endoscope of claim 1 wherein the long pass filter is maintained upstream in the light path from the wavelength selection filter and the wavelength ratio scaling filter.

6. An endoscope for directly transmitting an image from an in vivo target tissue to a user, the endoscope comprising:

a body including a proximal end and a distal end, the body being configured to position the distal end proximate to the target tissue;

a light emitter proximate to the distal end to direct an illumination light to the target tissue;

an eyepiece ocular coupled to the body at the proximal end that is sized to fit a human eye;

at least one collection light guide including a collector to receive emanating light from the target tissue and a conductor to conduct the emanating light along at least a portion of a light path to the eyepiece ocular which transmits the emanating light to the eye, wherein the user is able to directly view the target tissue directly through the eyepiece ocular without a transduction imaging device between the target tissue and the user;

a wavelength selection filter aligned with the collection light guide to be disposed in the light path, the wavelength selection filter selectively transmitting at least two desired wavelength bands of the emanating light; and a wavelength ratio scaling filter aligned with the collection light guide to be disposed in the light path, the wavelength ratio scaling filter selectively controlling the intensity of at least one of the desired wavelength bands, wherein the wavelength ratio scaling filter is variable, the wavelength selection filter and the wavelength ratio scaling filter manipulating the emanating light from the target tissue to selectively enhance an image of the target tissue.

7. The endoscope of claim 6 wherein the wavelength ratio scaling filter is continuously variable.

8. A method for a user to directly view a target tissue through an endoscope, the method comprising:

a) illuminating the target tissue by emitting illumination light from a distal end of the endoscope to the target tissue under conditions suitable to thereby cause light to emanate from the target tissue to provide an emanating light;

b) collecting the emanating light that contacts the distal end of a light collection system maintained in the endoscope;

c) conducting the emanating light along a light path from the distal end of the endoscope to an eyepiece ocular at the proximal end that is sized to fit a human eye, wherein such conducting comprises transmitting the emanating light through a light collection system comprising a wavelength selection filter that selectively transmits at least two desired wavelength bands of the emanating light and a wavelength ratio scaling filter that selectively controls the intensity of at least one of the desired wavelength bands to provide a filtered light representation of the target tissue; and d) viewing the filtered light representation of the target tissue through the eyepiece ocular, wherein the illumination light transmitted to the target tissue consists essentially of a selected wavelength band and the light collection system further comprises a long pass filter disposed in the light path, wherein the long pass filter blocks light having about the same wavelength as the selected wavelength band and transmits other light.

9. A method for a user to directly view a target tissue through an endoscope, the method comprising:

a) illuminating the target tissue by emitting illumination light from a distal end of the endoscope to the target tissue under conditions suitable to thereby cause light to emanate from the target tissue to provide an emanating light, wherein the illumination light is transmitted through a band pass filter maintained at the distal end of the endoscope, wherein the band pass filter transmits a selected wavelength band of light and blocks other light;

b) collecting the emanating light that contacts the distal end of a light collection system maintained in the endoscope;

c) conducting the emanating light along a light path from the distal end of the endoscope to an eyepiece ocular at the proximal end that is sized to fit a human eye, wherein such conducting comprises transmitting the emanating light through a light collection system comprising a wavelength selection filter that selectively transmits at least two desired wavelength bands of the emanating light and a wavelength ratio scaling filter that selectively controls the intensity of at least one of the desired wavelength bands to provide a filtered light representation of the target tissue; and d) viewing the filtered light representation of the target tissue through the eyepiece ocular, wherein the illumination light transmitted to the target tissue consists essentially of a selected wavelength band and the light collection system further comprises a long pass filter disposed in the light path, wherein the long pass filter blocks light having about the same wavelength as the selected wavelength band and transmits other light.

10. A method for a user to directly view a target tissue through an endoscope, the method comprising:

a) illuminating the target tissue by emitting illumination light from a distal end of the endoscope to the target tissue under conditions suitable to thereby cause light to emanate from the target tissue to provide an emanating light, wherein the target tissue is illuminated by emitting the illumination light to the target tissue from a light source maintained at the distal end of the endoscope and;

b) collecting the emanating light that contacts the distal end of a light collection system maintained in the endoscope;

c) conducting the emanating light along a light path from the distal end of the endoscope to an eyepiece ocular at the proximal end that is sized to fit a human eye, wherein such conducting comprises transmitting the emanating light through a wavelength selection filter that selectively transmits at least two desired wavelength bands of the emanating light and through a wavelength ratio scaling filter that selectively controls the intensity of at least one of the desired wavelength bands to provide a filtered light representation of the target tissue; and d) viewing the filtered light representation of the target tissue through the eyepiece ocular, wherein the illumination light is selected to cause a detectable response in an exogenous fluorophore in a desired drug potentially found in the target tissue, and the viewing comprises determining the presence or amount of the drug in the tissue.

11. An endoscope for directly transmitting an image without transduction from an in vivo target tissue to a user, the endoscope comprising: a proximal end and a distal end and an elongated body therebetween; a light emitter at the distal end able to emit illumination light consisting essentially of blue light to the target tissue; a light collection system able to collect emanating light that contacts the distal end and conduct the emanating light along a light path to an eyepiece ocular at the proximal end that is sized to fit a human eye, wherein the light collection system comprises at least one collection light guide able to conduct the emanating light along at least a portion of the light path, a long pass filter disposed at the distal end of the collection light guide and that substantially blocks blue light, a wavelength selection filter disposed in the light path and able to selectively transmit at least two desired wavelength bands of the emanating light, and a wavelength ratio scaling filter disposed in the light path and able to selectively control the intensity of at least one of the desired wavelength bands, and wherein the user is able to directly view the target tissue through the eyepiece ocular without an imaging device between the target tissue and the user.

12. The endoscope of claim 11 wherein the illumination light is conducted from a light source maintained at the proximal end of the endoscope to the light emitter at the distal end of the endoscope via the illumination light guide, and wherein a band pass filter that transmits substantially only blue light is disposed at the distal end of the illumination light guide.

13. The endoscope of claim 11 wherein the light emitter comprises a light source disposed at the distal end of the endoscope.

14. A filter assembly for a scope to transmit an image from an in vivo target tissue to a user, comprising:

a casing including a proximal end with a first opening to receive a proximal section of the scope, a distal end with a second opening to receive a distal section of the scope, and a transmission passage extending between the first and second openings, the transmission passage being configured to transmit light along a light path from the distal end to the proximal end of the casing;

a rotatable housing attached to the casing, the rotatable housing including a knob configured to be gripped by a user and a filter holder positioned in the casing, the filter holder having at least one window; and at least one filter received in the at least one window, the housing rotating within the casing to position the at least one filter in alignment with the light path for selectively enhancing an image of the target tissue.

15. The filter assembly of claim 14 wherein at least one of the filters disposed within the at least one wall of the filter assembly is able to transmit at least two discrete desired wavelength bands of the light.

16. The filter assembly of claim 15 wherein the filter assembly comprises at least two of the housings, at least one housing having a wavelength selection filter disposed in the light path that is able to selectively transmit the at least two discrete desired wavelength bands, and at least one housing having a wavelength ratio scaling filter disposed in the light path and able to selectively control the intensity of at least one of the desired wavelength bands.

17. The filter assembly of claim 15 wherein the filter assembly further comprises a non-rotatable lens that maintains the sharpness of an image being transmitted along the light path and disposed in the light path within the housing.

18. The filter assembly of any one of claim 14, 15 or 16 wherein the filter assembly is sized to be placed within an endoscope.

19. The filter assembly of claim 14 wherein the filter assembly is included in an endoscope according to any one of claims 1, 2, 3, 4, 3, 6, or 7.

20. The filter assembly of claim 15 wherein the filter assembly is included in an endoscope according to any one of claims 1, 2, 4, 5, 3, 6, or 7.

21. The filter assembly of claim 16 wherein the filter assembly is included in an endoscope according to any one of claims 1, 2, 4, 5, 3, 6, or 7.

* * * * *